United States Patent
Koike et al.

(10) Patent No.: US 7,358,363 B2
(45) Date of Patent: Apr. 15, 2008

(54) ZINC COMPLEXES CAPABLE OF CAPTURING SUBSTANCES HAVING ANIONIC SUBSTITUENTS

(75) Inventors: Tohru Koike, 19-18, Ushitahigashi 2-chome, Higashi-ku, Hiroshima-shi, Hiroshima 732-0063 (JP); Masatatsu Suzuki, Kanazawa (JP); Mitsuhiko Shionoya, Matsudo (JP)

(73) Assignee: Tohru Koike, Hiroshima (JP)

( * ) Notice: Subject to any disclaimer, the term of this patent is extended or adjusted under 35 U.S.C. 154(b) by 411 days.

(21) Appl. No.: 10/878,131

(22) Filed: Jun. 21, 2004

(65) Prior Publication Data
US 2005/0038258 A1 Feb. 17, 2005

Related U.S. Application Data

(63) Continuation of application No. PCT/JP02/13341, filed on Dec. 20, 2002.

(30) Foreign Application Priority Data
Dec. 21, 2001 (JP) ............................. 2001-390395

(51) Int. Cl.
*C07D 471/22* (2006.01)
(52) U.S. Cl. ...................................... 546/27
(58) Field of Classification Search ............... 546/27, 546/255
See application file for complete search history.

(56) References Cited

U.S. PATENT DOCUMENTS
5,874,584 A 2/1999 Wear et al.

FOREIGN PATENT DOCUMENTS
| JP | 8-506846 A | 7/1996 |
| JP | 11-057695 A | 3/1999 |
| JP | 2001-253871 A | 9/2001 |
| WO | WO 94/19379 A1 | 9/1994 |

OTHER PUBLICATIONS

M. Yashiro et al, "Preparation and Study of Dinuclear Zinc(II) Complex for the Efficient Hydrolysis of the Phosphodiester Linkage in a Diribonucleotide", *J. of Chem. Soc., Chem Commun.*, No. 17, pp. 1793-1794 (1995).

K. Yamaguchi et al, "Hydrolysis of phosphodiester with hydro- or carboxylate-bridged dinuclear Ni(II) and Cu(II) complexes", *Chem. Commun.*, No. 4, pp. 375-376 (2001).

S. Nishino et al, "Enhanced Nucleophilicity and Depressed Electrophilicity of Peroxide by Zinc(II), Aluminum (III) and Lanthanum(III) Ions", *Zeitschrift fuer Naturforschung C: J. of Biosciences*, vol. 56, No. 1/2, pp. 138-143 (Feb. 2001).

J. Sato et al, "Properties of chiral Ce(III) tppn complex as chiral shift reagent in aqueous solution", *Rare Earths*, No. 32, pp. 58-59 (1998).

H. Adams et al, Zinc(II) complexes of tetrapodal ligands derived from tetra-substituted 1,n-diaminoalcohols, *J. of Chem. Soc., Dalton Trans.*, No. 6, pp. 925-930 (Feb. 2002).

*Primary Examiner*—Zinna N. Davis
(74) *Attorney, Agent, or Firm*—Frishauf, Holtz, Goodman & Chick, P.C.

(57) ABSTRACT

A zinc complex represented by formula (I-0):

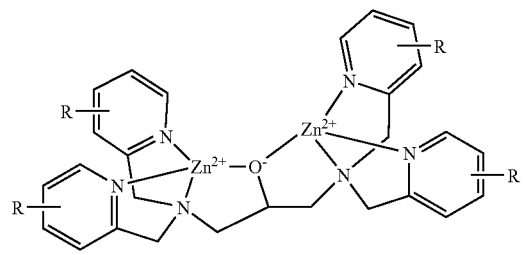

(I-0)

{wherein R may be the same or different from each other and represents H; an alkyl group having 1 to 16 carbon atoms; an acyl group, a carboxyalkyl group, an acylalkyl group, a carbamoylalkyl group, a cyanoalkyl group, a hydroxyalkyl group, an aminoalkyl group or a haloalkyl group (here, a carbon number at an alkyl portion of these groups is 1 to 16); a carboxyl group; a carbamoyl group; a hydroxyl group; a cyano group; an amino group or; a halogeno group (provided that all are Hs are excluded)} which is capable of capturing a substance having an anionic substituent.

1 Claim, 16 Drawing Sheets

NP²⁻–Zn₂L (o-methyl type)

A⁻–Zn₂L (o-methyl type)

NP$^{2-}$–Zn$_2$L  (H type)

A$^-$–Zn$_2$L  (H type)

Phosphorylated serine

Ser-P

Phosphorylated threonine

Thr-P

Phosphorylated tyrosine

Tyr-P

③

④ M+Na divalent

⑤ M+H divalent

ZINC COMPLEXES CAPABLE OF CAPTURING SUBSTANCES HAVING ANIONIC SUBSTITUENTS

This application is a continuation application of International Application PCT/JP02/13341 filed Dec. 20, 2002.

FIELD OF THE INVENTION

The present invention relates to a novel zinc complex capable of capturing a substance having an anionic substituent, and a capturing agent for a substance having an anionic substituent, a deactivating agent for phosphorylated substance, a phosphatase inhibitor, an additive for mass spectrometry, an additive for electrophoresis, an additive for nuclear magnetic resonance, and an additive for chromatography, a method for preparing a zinc complex, a method for capturing a substance having an anionic substituent, and a method for analyzing a substance having an anionic substituent, each utilizing the zinc complex.

BACKGROUND ART

As methods for analyzing phosphorylated substances, for example, phosphorylated biological substances, a method using enzyme-linked immunosorbent assay and a method using a radioisotope have conventionally been known. In the analysis of phosphorylated biological substances, a substance is desired which has a property such that the substance strongly binds to a phosphate monoester dianion as an anionic substituent under predetermined conditions and a property such that the resultant complex is detectable, and which is safe and inexpensive.

As a method for lowering the phosphate concentration of waste water, there is a method using a composite metal hydroxide disclosed in Japanese Unexamined Patent Publication No. Hei. 11-57695. In the field of medicine, as a substance used for the medical treatment of hyperphosphatemia, there is a polymer having a guanidino group disclosed in Japanese Unexamined Patent Publication No. Hei. 8-506846. A substance is desired which binds more strongly to phosphate and which is safer and more inexpensive than the composite metal hydroxide or a polymer having a guanidino group.

However, such a substance has not been known, which strongly binds to a phosphate monoester dianion to form a complex detectable and which is safe and inexpensive.

The enzyme-linked immunosorbent assay, which is one of the methods for analyzing a phosphorylated biological substance, utilizes the action of an antibody which specifically binds to a desired substance. Therefore, there is a need to prepare an antibody specific to the desired substance. The preparation of the antibody has a problem in that a great amount of the desired substance must be purified and obtained. In addition, the preparation of the antibody uses immune response of an animal and hence causes a problem in that a prolonged period of time is required to prepare the same. Further, an antibody for a phosphorylated site in a molecular structure with several kDa (daltons) or less cannot be prepared, and therefore a problem arises in that a phosphorylated biological substance having such a small molecular structure cannot be analyzed by enzyme-linked immunosorbent assay.

In the method for analyzing a phosphorylated biological substance using a radioisotope, radioisotope $^{32}P$ is used. Therefore, there is a disadvantage in that handling of radiation in laboratories and management of waste liquor are cumbersome.

Further, the composite metal hydroxide used for lowering the phosphate concentration of waste water and the polymer having a guanidino group used for the medical treatment of hyperphosphatemia individually have only a poor ability to bind to a phosphate group. Therefore, for capturing a certain amount of a phosphate, a large amount of the composite metal hydroxide or the polymer having a guanidino group must be used as a phosphate-group bind substrate.

In view of the above problems accompanying the prior art, the present invention has been made, and an object is to provide a safe and inexpensive substance which binds to an anionic substituent, especially a phosphate monoester dianion under predetermined conditions to form an easily detectable substance having the substituent, and to provide a substance applying the above binding, a substance capable of quickly and easily capturing a phosphorylated substance, and a capturing method as well as a method for detecting the captured substance.

DISCLOSURE OF THE INVENTION

The present inventors have synthesized a novel zinc complex (binuclear zinc complex). Further, the present inventors have found that a certain zinc complex (including the above novel zinc complex) binds to an anionic substituent, especially strongly binds to a phosphate monoester dianion under neutral conditions, and the following inventions have been completed.

The present invention (1) is a novel zinc complex represented by the following formula (I-0):

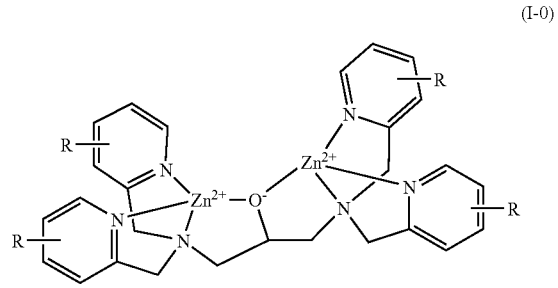

{wherein R's may be the same or different from each other and each represents H; an alkyl group having 1 to 16 carbon atoms; an acyl group, a carboxyalkyl group, an acylalkyl group, a carbamoylalkyl group, a cyanoalkyl group, a hydroxyalkyl group (e.g., a hydroxymethyl group), an aminoalkyl group (e.g., an aminomethyl group) or a haloalkyl group (here a carbon number at an alkyl portion of these groups is 1 to 16); a carboxyl group; a carbamoyl group; a hydroxyl group; a cyano group; an amino group or; a halogeno group (provided that the case where all are H's is excluded)}.

In the above construction, the zinc complex of the present invention has a binuclear zinc complex structure cross-linked with an alkoxide, and binds to an anionic substituent. As a result, by using the zinc complex of the present invention, various types of substances having an anionic substituent can be quickly and easily analyzed and separated.

As an example of the novel zinc complex represented by formula (I-0), there can be mentioned one in which each of R's is a methyl group at the sixth position, represented by the following formula (Ib):

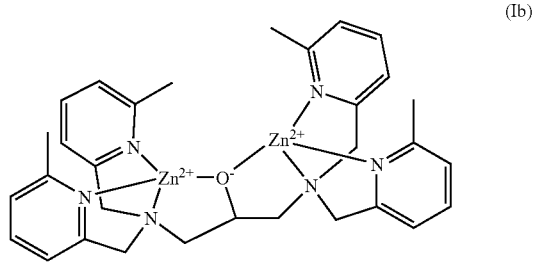

(Ib)

This zinc complex can be easily synthesized at a low cost by the method described in the Examples below. This zinc complex binds to an anionic substituent. Therefore, by using the zinc complex which can be easily synthesized at a low cost, various types of substances having an anionic substituent can be quickly and easily analyzed and separated. Formula (I') below is a formula which assigns numerals to the positions of rings in formula (I-0) above or formula (I) below, and the sixth position in formula (I-0) or formula (I) corresponds to the position indicated by numeral 6 in formula (I').

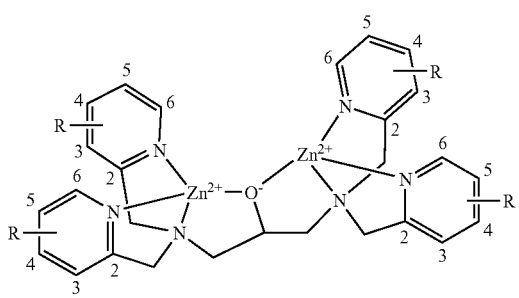

(I')

The present invention (2) is a capturing agent for a substance having an anionic substituent, wherein the capturing agent comprises a zinc complex (binuclear zinc complex) represented by the following formula (I):

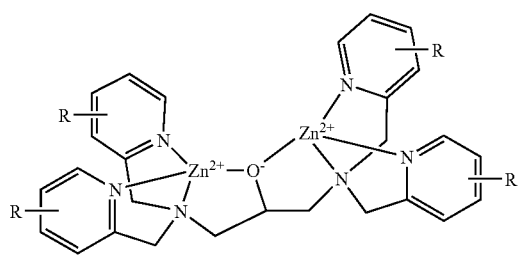

(I)

{wherein R's may be the same or different from each other and each represents H; an alkyl group having 1 to 16 carbon atoms; an acyl group, a carboxyalkyl group, an acylalkyl group, a carbamoylalkyl group, a cyanoalkyl group, a hydroxyalkyl group (e.g., a hydroxymethyl group), an aminoalkyl group (e.g., an aminomethyl group) or a haloalkyl group (here a carbon number at an alkyl portion of these groups is 1 to 16); a carboxyl group; a carbamoyl group; a hydroxyl group; a cyano group; an amino group or; a halogeno group}. The above-mentioned zinc complex has a property such that it binds to an anionic substituent, and therefore it can quickly and easily capture the substance having an anionic substituent. In addition, the above-mentioned capturing agent can be used for capturing a substance having an anionic substituent in a solution to separate the substance having an anionic substituent from a solvent. Further, the above-mentioned capturing agent can also be used for quantitatively determining a substance having an anionic substituent.

As an example of the zinc complex represented by formula (I), there can be mentioned one in which each of R's is hydrogen, represented by the following formula (Ia):

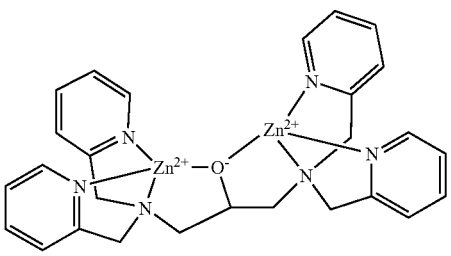

(Ia)

This zinc complex can be easily synthesized at a low cost by the method described in the Examples below. The zinc complex binds to an anionic substituent. As a result, by using the zinc complex which can be easily synthesized at a low cost, various types of substances having an anionic substituent can be quickly and easily analyzed and separated. The zinc complex of formula (Ia) is advantageously used not only in the present invention (2) but also in various kinds of applications of the following present inventions (3) to (9).

The present invention (3) is the capturing agent of the invention (2) above, wherein the substance having an anionic substituent is a phosphorylated substance. The zinc complex of the present invention has a property such that it strongly binds to a phosphate monoester dianion which is one of anionic substituents. As a result, a capturing agent, which quickly and easily captures a phosphorylated substance utilizing binding of the zinc complex to the phosphate monoester dianion, can be obtained. In addition, the capturing agent can be used for capturing a phosphorylated substance in a solution to separate the phosphorylated substance from a solvent. Further, the capturing agent can also be used for quantitatively determining a phosphorylated substance.

The present invention (4) is a deactivating agent for phosphorylated substance, comprising the zinc complex of formula (I) in the invention (2) above. The zinc complex contained in the phosphorylated-substance deactivating agent strongly binds to a phosphate monoester dianion. Therefore, the above-mentioned zinc complex binds to a phosphorylated site. The above-mentioned zinc complex covers, i.e., caps the phosphorylated site using the binding, and the capping suppresses a reaction between a substance having the phosphorylated site and another substance, thus making it possible to lower the biological activity of the phosphorylated substance.

The present invention (5) is a phosphatase inhibitor comprising the zinc complex of formula (I) in the invention (2) above. The zinc complex contained in the phosphatase inhibitor strongly binds to a phosphate monoester dianion. By virtue of such a property, the zinc complex contained in the phosphatase inhibitor binds to a phosphorylated site of a protein or a nucleotide to cap the phosphorylated site. The capping temporarily inhibits a phosphatase from functioning. As a result, by using the phosphatase inhibitor, presence or absence of a novel phosphatase and its enzyme activity can be examined.

The present invention (6), the present invention (7), the present invention (8), and the present invention (9) are, respectively, an additive for mass spectrometry, an additive for electrophoresis, an additive for nuclear magnetic resonance, and an additive for chromatography, each comprising the zinc complex of formula (I) in the invention (2) above.

The zinc complex contained in each additive for analysis has a property such that it binds to an anionic substituent, especially strongly binds to a phosphate monoester dianion. Further, the binding can be found by a conventional analysis method. As a result, the additive for analysis of the present invention can be used in analysis of a substance having an anionic substituent or a phosphate monoester dianion by a conventional method.

The present invention (10) is a method for preparing the zinc complex of formula (I) in the invention (2) above, wherein the method comprises the steps of: adding zinc ions (e.g., in the form of a zinc salt) to a solution of a polyamine ligand; adjusting the resultant solution to be neutral; and then concentrating the solution. According to the present invention, a zinc complex can be obtained by a simple method comprising adding (divalent) zinc ions to a solution of a polyamine ligand, and rendering the resultant solution neutral and then concentrating it. Zinc ions are easily available by, for example, dissolving a zinc salt. As a result, in addition to the above-mentioned effects of the invention, a zinc complex can be further easily synthesized.

The present invention (11) is the method of the invention (10) above, wherein the polyamine ligand is represented by the following formula (II):

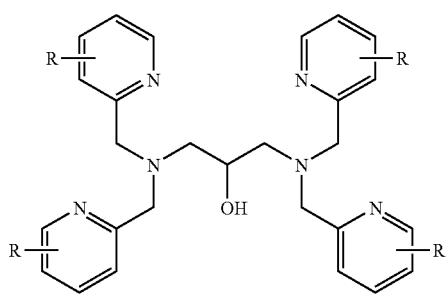

(II)

{wherein R's are as defined above for the formula in the invention (2).} For example, the polyamine ligand in which each of R's is hydrogen is N,N,N',N'-tetrakis((2-pyridyl)methyl)-1,3-diamino-2-hydroxypropane (hereinafter, referred to as "TPAHP"), and the polyamine ligand in which each of R's is a methyl group at the sixth position is N,N,N',N'-tetrakis((6-methyl-2-pyridyl)methyl)-1,3-diamino-2-hydroxypropane (hereinafter, referred to as "TMAHP"). These can be obtained easily and at a low cost. The structures of TPAHP {formula (IIa)} and TMAHP {formula (IIb)} are shown below.

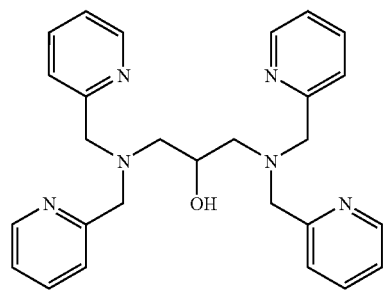

(IIa)

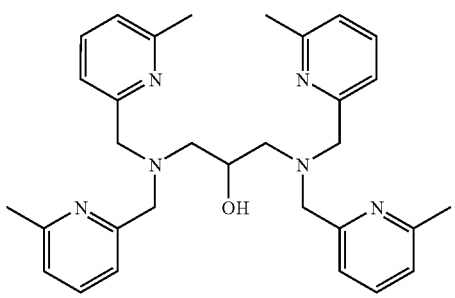

(IIb)

The present invention (12) is the method of the invention (10) above, wherein the polyamine ligand is N,N,N',N'-tetrakis((2-pyridyl)methyl)-1,3-diamino-2-hydroxypropane, that is, the invention (10) above wherein the polyamine ligand is TPAHP.

The present invention (13) is the method of any one of the inventions (10) to (12) above, wherein zinc acetate is used as a source of zinc ions. When zinc acetate is used as a source of zinc ions, the resultant zinc complex has a form being bound to one molecule of acetate anion. As a result, the zinc complex is a stable complex at room temperature, which can be easily stored in the state of a concentrated solution in a laboratory. Thus, storage of the zinc complex is easy.

The present invention (14) is a method for capturing a substance having an anionic substituent, comprising allowing a substance having an anionic substituent to bind to the zinc complex of formula (I) in the invention (2) above to capture it. In the present invention, a substance having an anionic substituent is captured by allowing the substance to bind to the zinc complex. The zinc complex can be used in the form of, for example, being carried on a certain support. As a result, using a support selected according to the scale or form of the capturing, the substance having an anionic substituent can be captured.

The present invention (15) is the method of the invention (14) above, wherein the substance having an anionic substituent is a substance having a phosphate monoester dianion. In the present invention, the substance having an anionic substituent is a substance having a phosphate monoester dianion. Examples of substances having a phosphate monoester dianion include phosphorylated substances. As a result, in addition to the above-mentioned effects of the method, a phosphorylated substance can be easily captured.

The present invention (16) is the method of the invention (14) or (15) above, which comprises the steps of: allowing the substance having an anionic substituent to bind to the zinc complex under neutral conditions; and then dissociating the substance having an anionic substituent from the zinc complex under acidic conditions. In the present invention, the substance having an anionic substituent is captured under neutral conditions, and the captured substance having an anionic substituent is dissociated from the zinc complex under acidic conditions. The reason that the substance having an anionic substituent can be captured and further the captured substance can be released resides in that the binding between the substance having an anionic substituent and the zinc complex is changed by pH. As a result, capturing of the substance having an anionic substituent can be easily conducted. Further, the capturing and recovery of the captured substance can be appropriately controlled by changing the pH conditions. In the present invention, the neutral conditions are conditions such that the upper limit of pH of the solution is 8 or less, preferably 7.5 or less, and the lower limit is 5 or more, preferably 5.5 or more. The acidic conditions are conditions such that the upper limit of pH of the solution is 4.5 or less, preferably 4 or less.

BRIEF DESCRIPTION OF THE DRAWINGS

In FIG. 12 (m/z 1,463.72 [M+3H]$^+$, m/z 1,485.65 [M+2H+Na]$^+$, m/z 1,501.64 [M+2H+K]$^+$), conditions for the measurement with respect to non-phosphorylated type ($C_{62}H_{92}N_{16}O_{25}^{2-}$; $^+H_2$-Thr-Ser-Thr-Glu-Pro-Gln-Tyr-Gln-Pro-Gly-Glu-Asn-Leu-O$^-$; Exact Mass: 1,460.64) p60c-src peptide 521-533 and phosphorylated type ($C_{62}H_{91}N_{16}O_{28}P^{4-}$; $^+H_2$-Thr-Ser-Thr-Glu-Pro-Gln-Tyr(PO$_3$H$_2$)-Gln-Pro-Gly-Glu-Asn-Leu-O$^-$; Exact Mass: 1,538.59) p60c-src peptide 521-533 are as follows: Matrix: THAP; experimental mode: Reflector; accelerating voltage: 20,000 V; grid voltage: 57.500%; laser intensity: 2,400; measurement times: 128; and degree of vacuum: 2.51e-07 mmHg.

In FIG. 13, conditions for the measurement with respect to p60c-src peptide 521-533 non-phosphorylated type and phosphorylated type Phos-tag complex ($C_{89}H_{120}N_{22}O_{29}PZn_2^-$; Exact Mass: 2,119.69; m/z 2,122.03 [M+2H]$^+$)

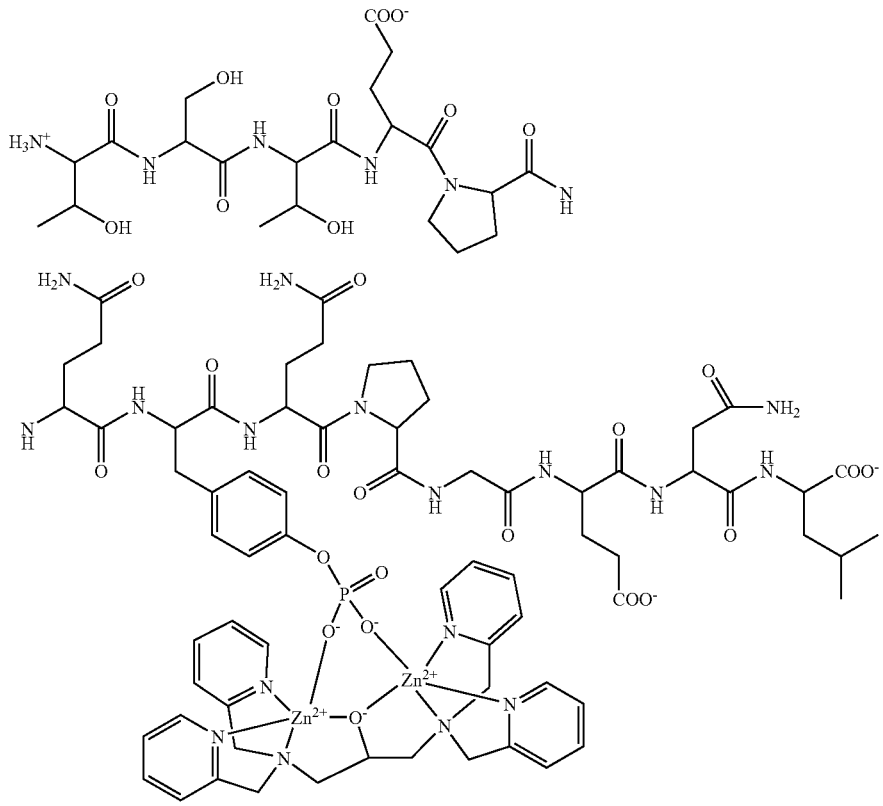

are as follows: Matrix: THAP; experimental mode: Reflector; accelerating voltage: 20,000 V; grid voltage: 57.500%; laser intensity: 2,400; measurement times: 128; and degree of vacuum: 2.82e-07 mmHg.

Figure 14:
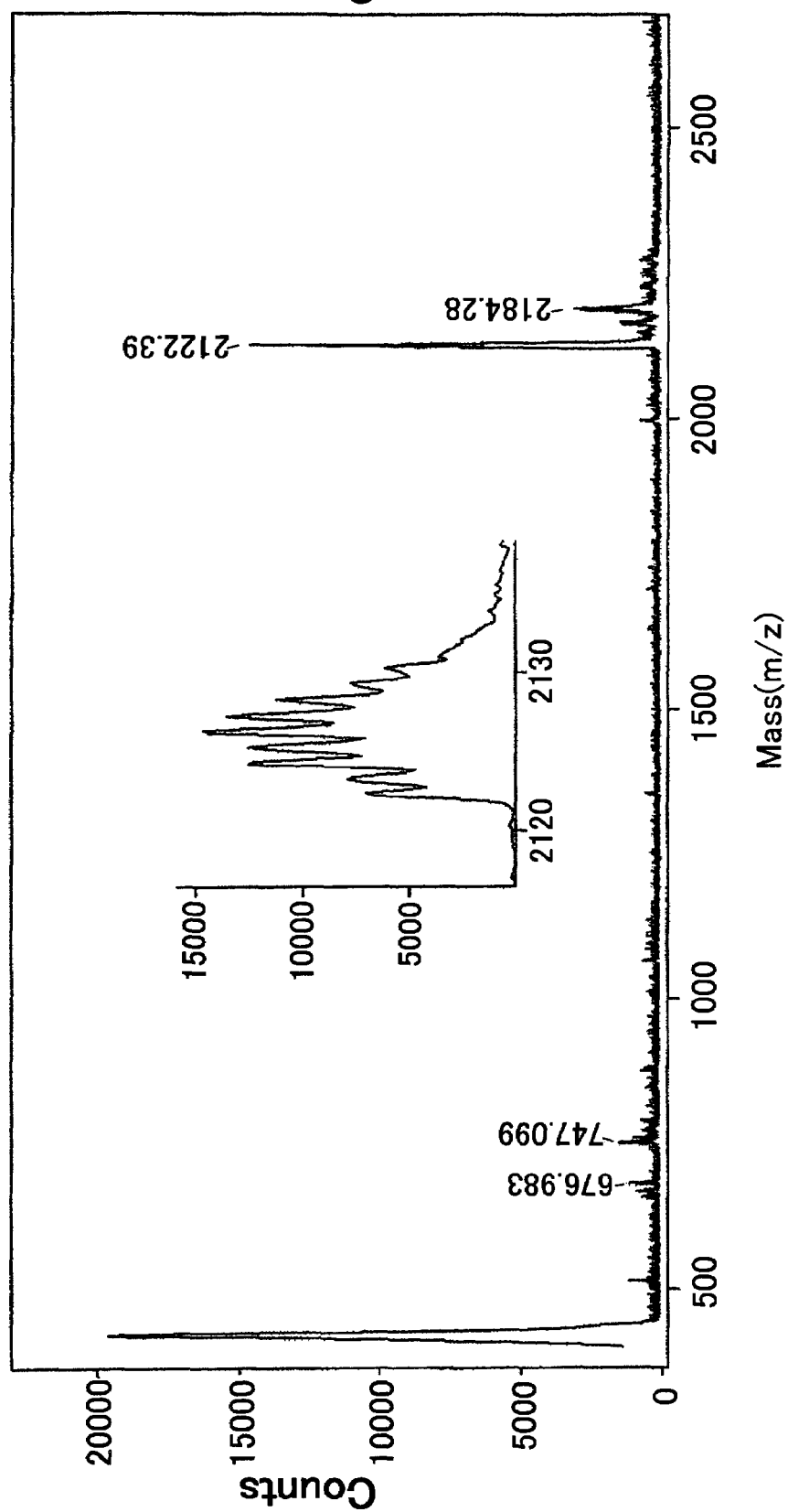

FIG. 14 is a diagram showing the results of MALDI-TOF/MS analysis with respect to a phosphorylated peptide to which the zinc complex of the present invention is added. In FIG. 14, conditions for the measurement with respect to the p60c-src peptide 521-533 phosphorylated type+Phos-tag complex (m/z 2,122.39 [M+2H]$^+$) are as follows: Matrix: THAP; experimental mode: Reflector; accelerating voltage: 20,000 V; grid voltage: 57.500%; laser intensity: 2,400; measurement times: 128; and degree of vacuum: 2.93e-07 mmHg.

Figure 15:
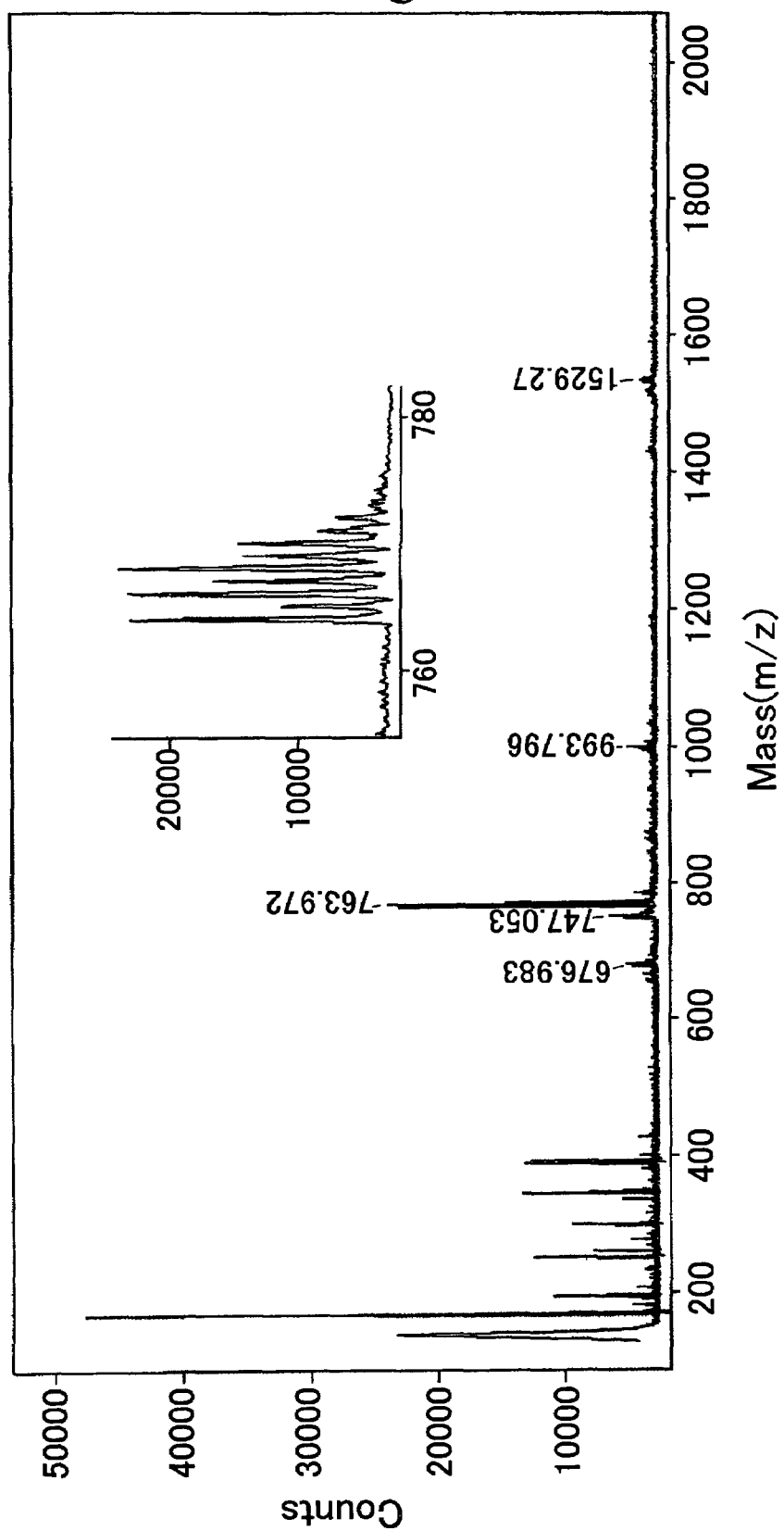

FIG. 15 is a diagram showing the results of MALDI-TOF/MS analysis with respect to O-phospho-L-serine to which the zinc complex of the present invention is added. In FIG. 15, conditions for the measurement with respect to the O-phospho-L-serine+Phos-tag complex ($C_{30}H_{35}N_7O_7PZn_2^+$; Exact Mass: 764.09; m/z 763.97 M$^+$)

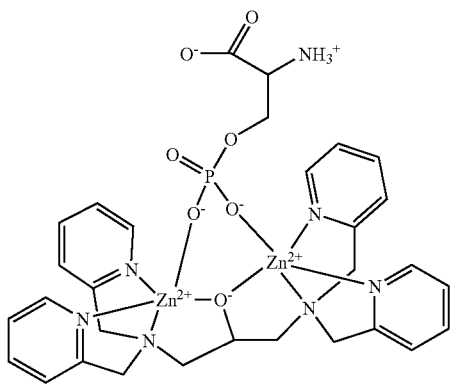

are as follows: Matrix: THAP; experimental mode: Reflector; accelerating voltage: 20,000 V; grid voltage: 57.500%; laser intensity: 2,350; measurement times: 128; and degree of vacuum: 2.47e-07 mmHg.

Figure 16:
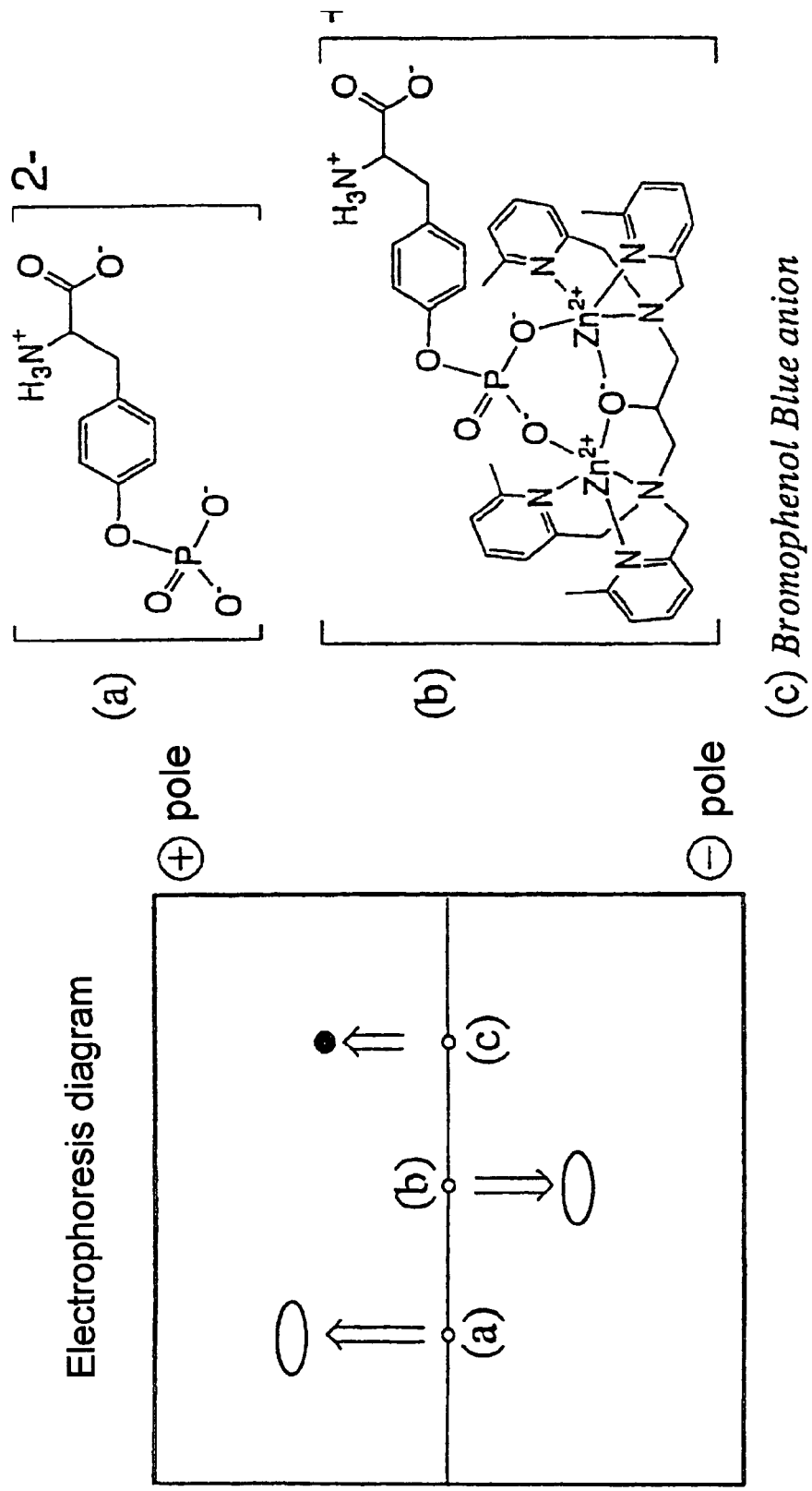

FIG. 16 is a diagram showing the results of electrophoresis with respect to the compound of the zinc complex (Ib) of the present invention bound to phosphorylated tyrosine.

Figure 17:
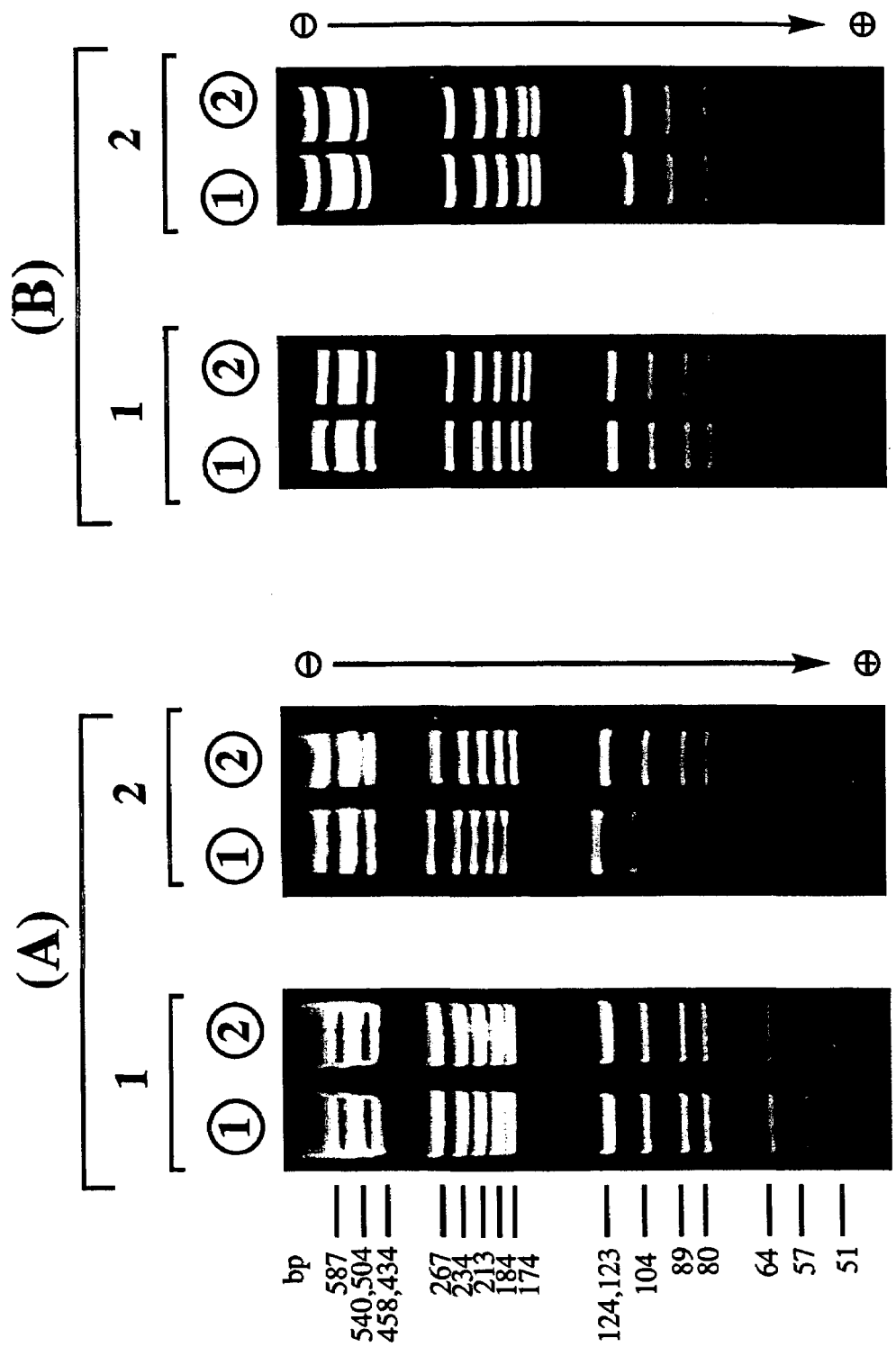

FIG. 17 is diagrams showing the results of electrophoresis with respect to DNAs having a phosphate group or having no phosphate group. In FIG. 17 concerning the polyacrylamide gel electrophoresis (10% gel) of double-stranded DNAs (pBR322 treated with restriction enzyme Hae III), (A) shows bands of a control {5'-phosphate (1①), 5'-OH (1②)} and Phos-tag 10 μM {5'-phosphate (2①), 5'-OH (2②)} when a 90 mM borate buffer are used, and (B) shows bands of a control {5'-phosphate (1①), 5'-OH (1②)} and Phos-tag 10 μM {5'-phosphate (2①), 5'-OH (2②)} when a 90 mM Tris-22.5 mM phosphate buffer are used.

Figure 18:
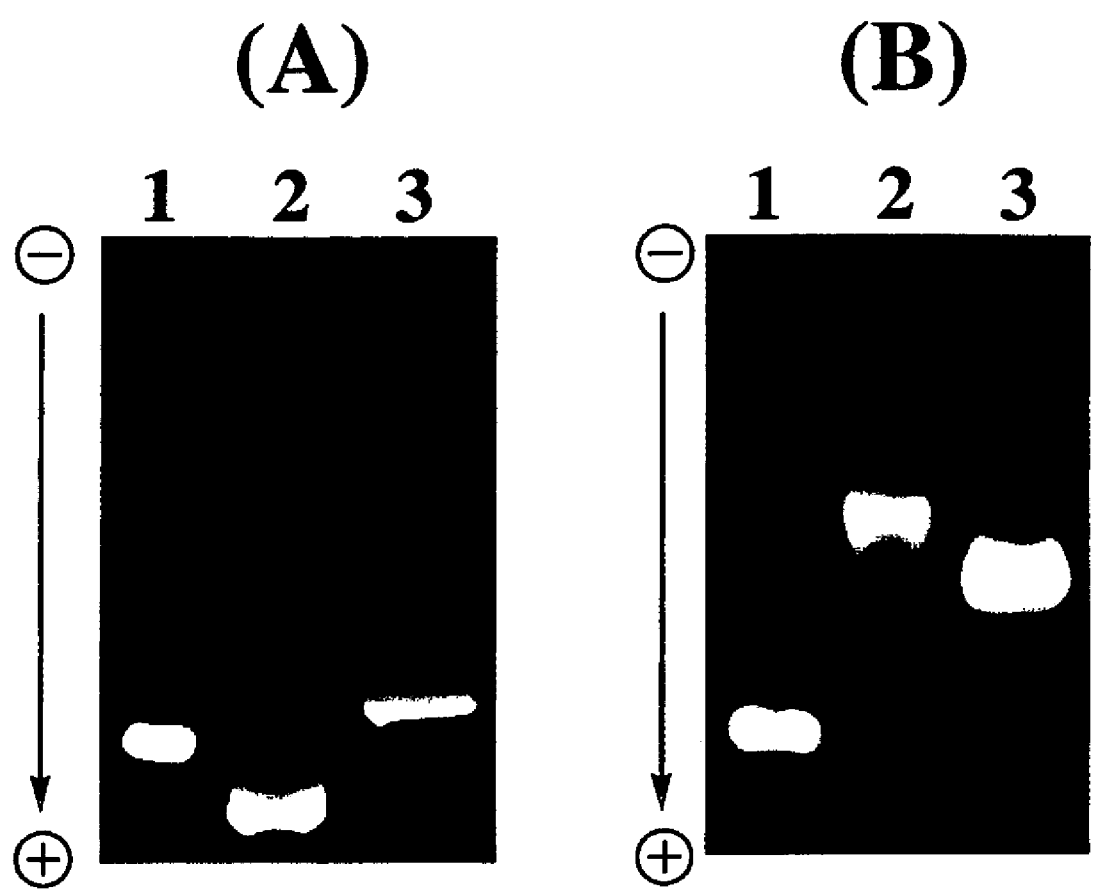

FIG. 18 is diagrams showing the results of electrophoresis showing the migration distance of the zinc complex. In FIG. 18, conditions for the measurement of Native-polyacrylamide gel electrophoresis (7.5% gel) are as follows: 40 mA, 1.5 hours, Coomassie Brilliant Blue staining, buffer for separation (lower gel buffer): 375 mM Tris-hydrochloric acid (pH 8.8); buffer for concentration (stacking gel buffer): 125 mM Tris-hydrochloric acid (pH 6.8), buffer for migration (running buffer): 25 mM Tris-hydrochloric acid (pH 8.4)+192 mM glycine. In FIG. 18, (A) shows a control, and (B) shows 20 μM Phos-tag, and lane 1 is a band of bovine serum albumin, lane 2 is a band of bovine $α_{s1}$-casein (eight serines are phosphorylated forms), and lane 3 is a band of bovine $α_{s1}$-casein (dephosphorylated form).

Figure 19:
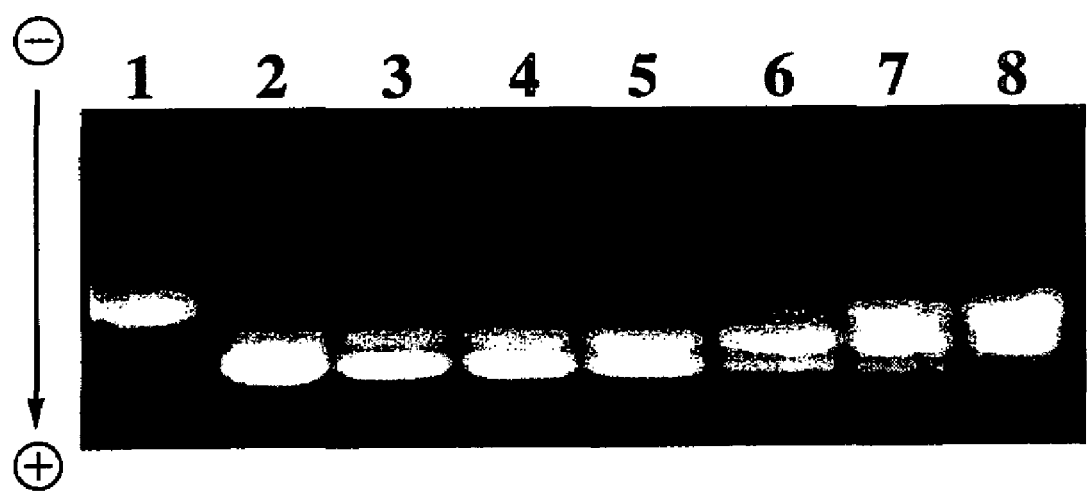

FIG. 19 is a diagram showing electrophoresis for explaining that the zinc complex serves as an enzyme inhibitor. In FIG. 19, conditions for the measurement of SDS-polyacrylamide gel electrophoresis (12.5% gel) are as follows: 40 mA, 1 hour, Coomassie Brilliant Blue staining, buffer for separation (lower gel buffer): 375 mM Tris-hydrochloric acid (pH 8.8), 0.1% (w/v) SDS, buffer for concentration (stacking gel buffer): 125 mM Tris-hydrochloric acid (pH 6.8), 0.1% (w/v) SDS; buffer for migration (running buffer): 25 mM Tris-hydrochloric acid (pH 8.3)+190 mM glycine, 0.1% (w/v) SDS. In FIG. 19, lane 1 is a band of bovine β-casein (phosphorylated form), lane 2 is a band of bovine β-casein (dephosphorylated form), and lanes 3 to 8 are bands of PAP hydrolysis products (3: 30 μM Phos-tag; 4: 40 μM Phos-tag; 5: 50 μM Phos-tag; 6: 100 μM Phos-tag; 7: 150 μM Phos-tag; 8: 200 μM Phos-tag).

BEST MODE FOR CARRYING OUT THE INVENTION

1. Synthesis of Zinc Complex

One embodiment of the present invention will be described hereinbelow. The present invention is not limited to these embodiments and can be changed or modified in various manners within the scope of the present invention.

The zinc complex according to the present embodiment is represented by formula (I) below. Particularly, when each of R's is hydrogen, the zinc complex is represented by formula (Ia), and, when each of R's is a methyl group at the sixth position, the zinc complex is represented by formula (Ib). A composite of the zinc complex of formula (I) and a substance having an anionic substituent (acetate anion here) is represented by formula (III) below. Particularly, a composite of the zinc complex of formula (Ia) and an acetate anion is represented by formula (IIIa), and a composite of the zinc complex of formula (Ib) and an acetate anion is represented by formula (IIIb).

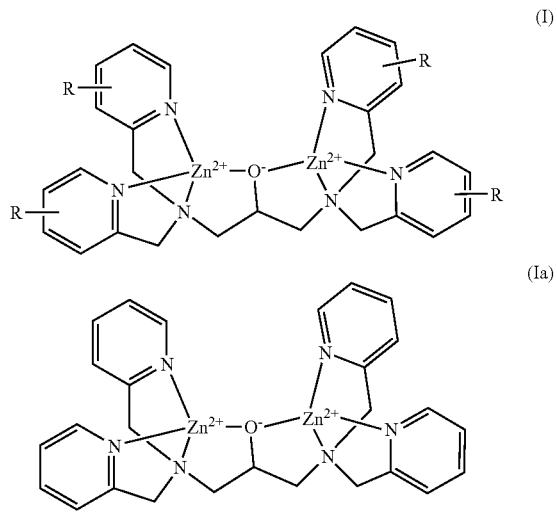

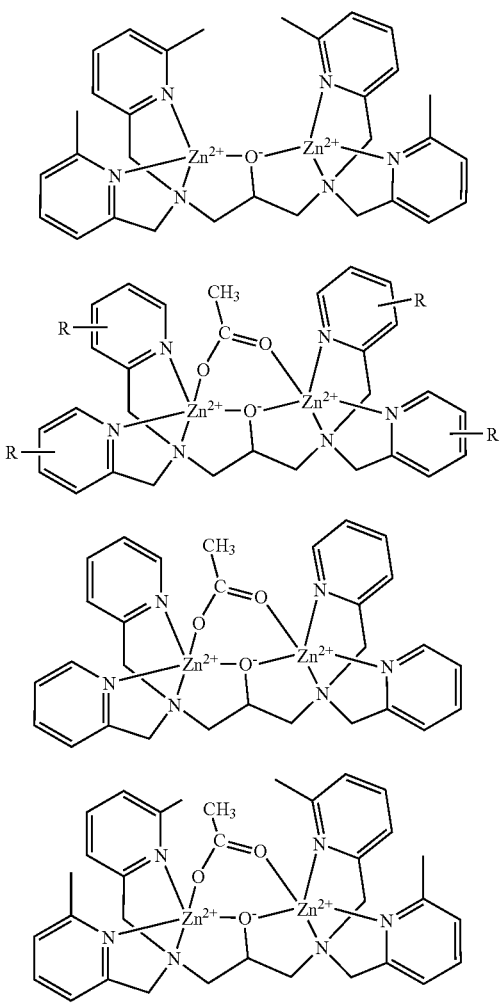

(Ib)

(III)

(IIIa)

(IIIb)

The above complex is obtained by adding zinc ions or a zinc salt to a solution of a compound of formula (II) below, which is a polyamine ligand, and then adjusting the resultant solution to be neutral and concentrating the solution adjusted.

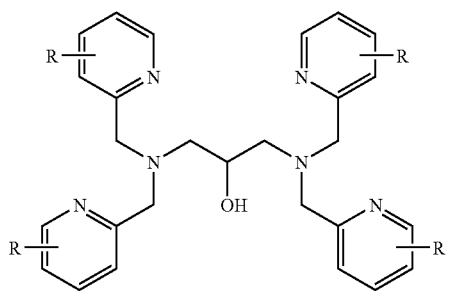

(II)

The wording "adjusting the resultant solution to be neutral" means that the solution is adjusted so that the upper limit of pH of the solution is 9 or less, preferably 7.5 or less, further preferably 7.2 or less, and the lower limit is 5 or more, preferably 6.5 or more, further preferably 6.8 or more. The "concentrating" means evaporating a solvent. As a solvent dissolving the compound of formula (II) and the zinc salt (zinc ions), for example, an alcohol, such as ethanol or methanol, can be employed. However, the solvent is not limited to an alcohol, and another aprotic polar solvent may be used.

When formula (II) corresponds to N,N,N',N'-tetrakis-((2-pyridyl)methyl)-1,3-diamino-2-hydroxypropane (TPAHP), the compounds of formulae (Ia) and (IIIa) can be obtained. TPAHP can be synthesized by the method described in literature (Bull. Chem. Soc. Jpn., 1990, Vol. 63, p. 1,115-1, 120). When formula (II) corresponds to N,N,N',N'-tetrakis ((6-methyl-2-pyridyl)methyl)-1,3-diamino-2-hydroxypropane (TMAHP), the compounds of formulae (Ib) and (IIIb) can be obtained. TMAHP can be synthesized by the method described in literature (J. Am. Chem. Soc., 1995, Vol. 117, p. 11,220-11,229).

The compound of formula (III) is a zinc complex ($A^-$-$Zn_2L$) comprising an acetate anion coordinated to the compound of formula (I). The compound of formula (III) can be synthesized by the method described in the Examples. The "$A^-$" denotes "$CH_3COO^-$", and the "L" denotes a portion (ligand) of formula (I) excluding two zinc ions ($Zn^{2+}$).

The compounds represented by formula (I) and formula (III) can be synthesized almost stoichiometrically utilizing relatively inexpensive compounds and general facilities for synthesis. As an example of a relatively inexpensive compound, there can be mentioned zinc acetate as a zinc salt.

As mentioned above, when zinc acetate is used as a source of zinc ions, the resultant complex has a form being bound to one molecule of acetate anion. As a result, the composite of formula (III) including formulae (IIIa) and (IIIb) is a stable complex at room temperature, which can be easily stored in the state of a concentrated solution in a laboratory, thus making storage of the complex easy. Further, the composites of formulae (IIIa) and (IIIb) can be obtained in the form of solid, together with counter anion. The solid has low toxicity and low hygroscopicity and hence is easy to store or handle.

In formulae (I) to (III), substituents R's may be the same or different, and each R represents H; an alkyl group having 1 to 16 carbon atoms (e.g., a methyl group); an acyl group, a carboxyalkyl group, an acylalkyl group, a carbamoylalkyl group, a cyanoalkyl group, a hydroxyalkyl group (e.g., a hydroxymethyl group), an aminoalkyl group (e.g., an aminomethyl group), or a haloalkyl group (wherein the alkyl portion of these groups has 1 to 16 carbon atoms); a caboxyl group; a carbamoyl group; a hydroxyl group; a cyano group; an amino group; or a halogeno group. From the viewpoint of facilitating preparation of the compound, it is preferred that all the R's in formulae (I) to (III) are the same substituent. Formula (II') is a formula which assigns numerals to the positions of rings in formula (II), and the sixth position in formula (II) corresponds to the position indicated by numeral 6 in formula (II').

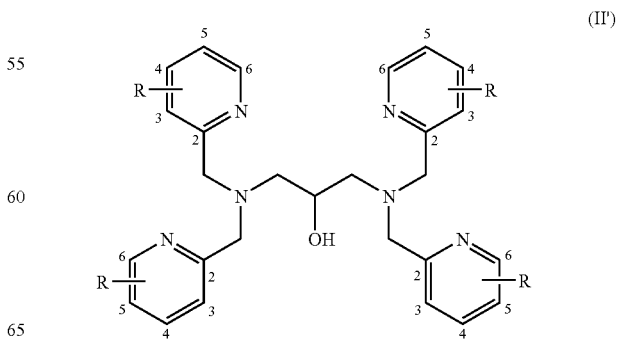

(II')

Introduction of substituent R into formula (I-0) or formula (I) can be achieved by first introducing a substituent to be introduced into formula (II). By a method used in synthesis of a pyridine derivative, substituent R shown in formula (II) can be the desired substituent. The method used in the synthesis of a pyridine derivative is, for example, a method described in '"Aromatic Amine Oxides", Eiji Ochiai, Elsevier Publishing Company, 1967', or '"Rodd's Chemistry Of Carbon Compounds" Vol. IV Part F, Elsevie Publishing Company, 1976'.

The zinc complex of formula (I) is stably present in the form of trivalent cation in a solution. Formula (Ib) corresponds to a zinc complex having a molecular weight of about 800 Da. The method for synthesizing the compounds represented by formula (Ib) and formula (IIIb) and the method for synthesizing the compounds represented by formula (Ia) and formula (IIIa) are shown in Example 1 and Example 2, respectively.

2. Properties of Complex

When the zinc complex of formula (I) is added to a solution of a substance having an anionic substituent under neutral conditions (under physiological conditions), the anionic substituent and the complex bind together. The binding is illustrated in FIG. 1.

Figure 1:
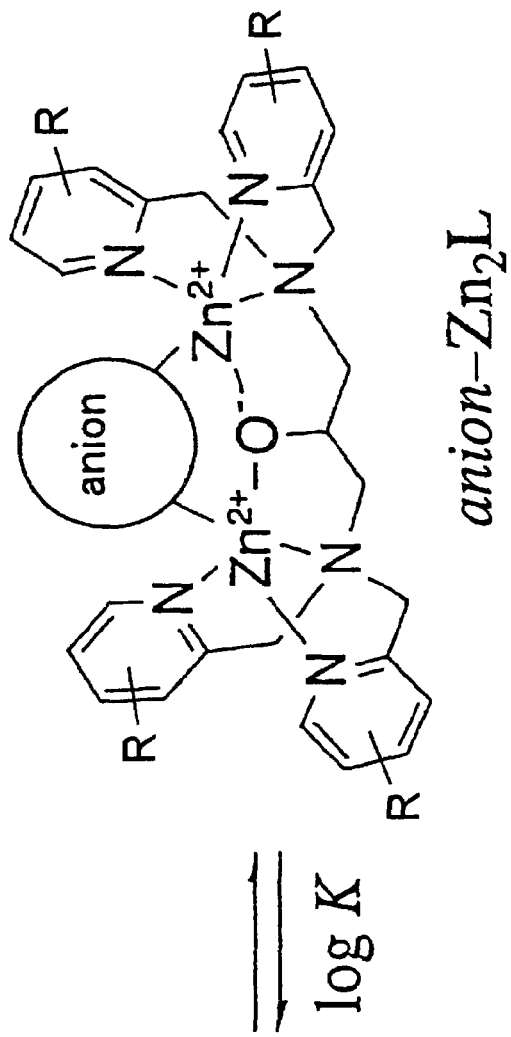
FIG. 1 is a view showing a general idea for capturing an anion by the zinc complex of formula (I).

In FIG. 1, "anion" denotes a substance having an anionic substituent, "$Zn_2L$" denotes the complex represented by formula (I), and "anion-$Zn_2L$" denotes a composite of the substance having an anionic substituent and the complex of formula (I) which bind together. Examples of anionic substituents include $-PO_3^{2-}$, $-COO^-$, $-OPO_3^{2-}$, $-SO_3^-$, $NO_3^-$, and $Cl^-$. When the system is made acidic conditions, the anionic substituent and the complex do not bind together.

Figure 2:
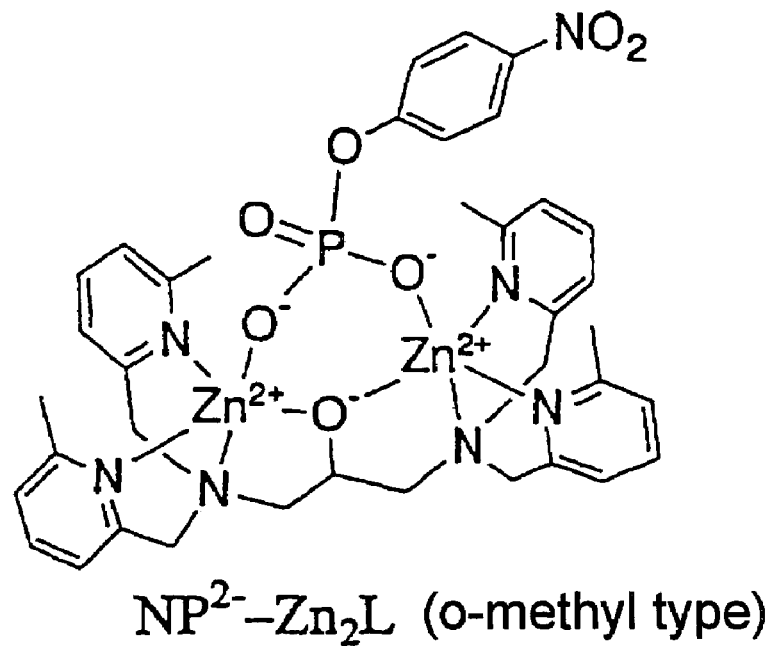
FIG. 2 is a view showing the binding of a 4-nitrophenylphosphate monoester anion and a zinc complex (formula Ib).
Figure 3:
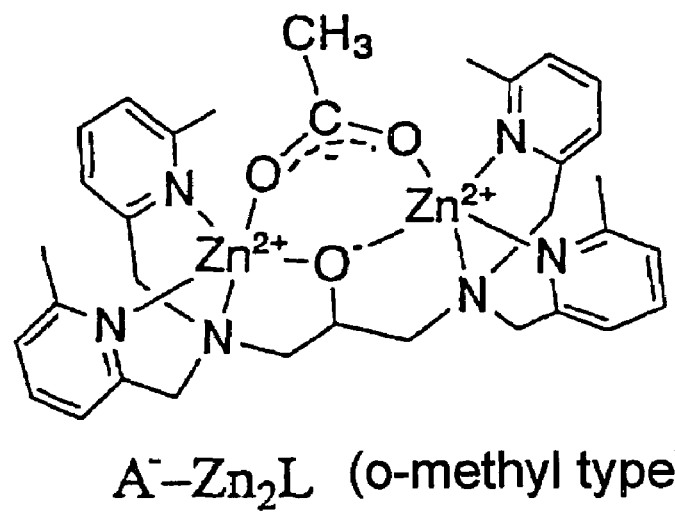
FIG. 3 is a view showing the binding of an acetate anion and a zinc complex (formula Ib).
Figure 4:
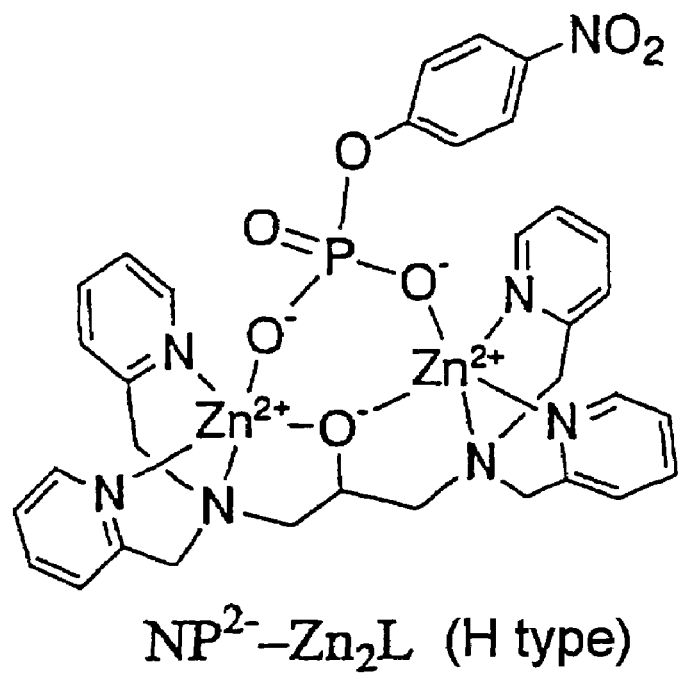
FIG. 4 is a view showing the binding of a 4-nitrophenylphosphate monoester anion and a zinc complex (formula Ia).
Figure 5:
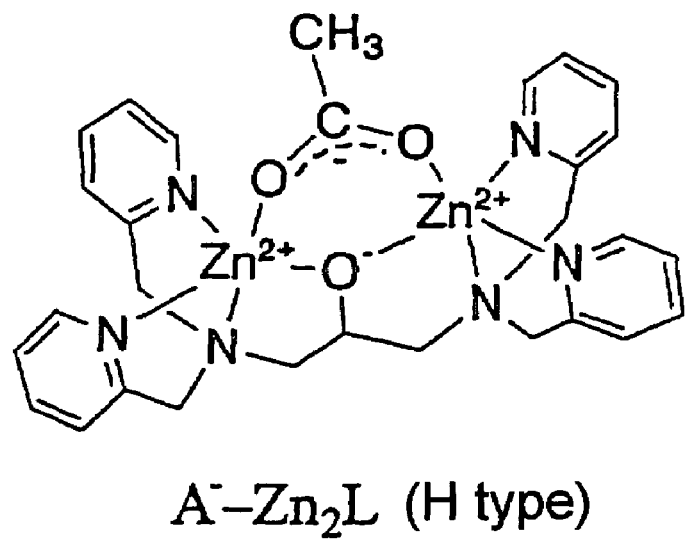
FIG. 5 is a view showing the binding of an acetate anion and a zinc complex (formula Ia).

Examples of composites of the above zinc complex and various anionic substituents are shown in FIGS. 2 to 5. FIG. 2 is a view showing the binding of a 4-nitrophenylphosphate monoester anion ($O_2NC_6H_4OPO_3^{2-}$) and the complex {$Zn_2L$ (o-methyl type)} represented by formula (Ib). FIG. 3 is a view showing the binding of an acetate anion and the complex {$Zn_2L$ (o-methyl type)} represented by formula (Ib). FIG. 4 is a view showing the binding of a 4-nitrophenylphosphate monoester anion ($O_2NC_6H_4OPO_3^{2-}$) and the complex ($Zn_2L$) {$Zn_2L$ (H type)} represented by formula (Ia). FIG. 5 is a view showing the binding of an acetate anion and the complex ($Zn_2L$) {$Zn_2L$ (H type)} represented by formula (Ia).

When the complex according to the present embodiment is added to a solution of a substance having a phosphate monoester dianion under neutral conditions, the phosphate monoester dianion and the complex bind together to form a composite. When the system is made acidic conditions, the phosphate monoester dianion and the complex do not bind together.

Conventionally, studies have been made on elucidation of the mechanism of action of phosphoesterase present in a living body. In the studies, it is stated that a number of phosphoesterases are activated by two metal ions (ions of, e.g., Zn, Ni, or Cu) {D. E. Wilcox, Chem. Rev. 96, 2435, (1996)}. In addition, studies have also been made on elucidation of the mechanism of hydrolysis of phosphate diester using a synthetic metal complex. However, the molecular structure required for selectively identifying phosphate monoester has not yet been elucidated. The complex according to the present embodiment can be the key to elucidate the molecular structure required for selectively identifying phosphate monoester.

3. Utilization of Complex (Capturing of Substance)

Using the complex according to the present embodiment as a component of a capturing agent, a substance having an anionic substituent can be captured. In addition, the use of the complex according to the present embodiment provides a method for capturing a substance having an anionic substituent. Examples of anionic substituents include substituents such as $-PO_3^{2-}$, $-COO^-$, $-OPO_3^{2-}$, $-SO_3^-$, $NO_3^-$, and $Cl^-$.

Using the complex according to the present embodiment as a component of a capturing agent, a substance having a phosphate monoester dianion can be captured. As examples of substances having a phosphate monoester dianion, there can be mentioned phosphorylated amino acid residues shown in FIGS. 6 to 8 and proteins having the amino acid residues. The complex according to the present embodiment strongly binds to a phosphate monoester dianion, and therefore the complex according to the present embodiment can capture a phosphorylated amino acid.

As mentioned above, the complex according to the present embodiment can be applied to phosphorylated amino acids, phosphorylated amino acid residues, and proteins having the amino acids. Phosphorylation and dephosphorylation of proteins are one of important themes of studies on the information transmission in living bodies and have close relation to the vital functions. In addition, elucidation of the process of such phosphorylation is a main task in the post-genome research, and has attracted attention as a target of drug preparation.

As an example of form of the complex used as a capturing agent, there can be mentioned a form of the complex carried on a support, such as a polymer film, a column support, or a plate pore. As an example of a method for forming the complex carried on a support, there can be mentioned a method in which a substituent (such as an amino group or a hydroxyl group) introduced into a pyridine skeleton, which is a ligand of the complex, is bound to a support, such as a polymer film, through a covalent bond using a cross-linking agent. In addition, as another example of the method for forming the complex carried on a support, there can be mentioned a method in which the complex is mixed into polymer raw materials as a binder and the resultant mixture is subjected to expansion and granulation. In capturing a substance by the capturing agent, a solution containing a substance to be captured is brought into contact with the capturing agent. The contact makes it possible to capture the substance to be captured. When the complex is carried on the above various supports, such as a polymer film, a column support, and a plate pore, the capturing agent can be in various forms. Thus, the capturing agent can be in various forms, and therefore the capturing agent can be appropriately selected according to the scale or form of the substance to be captured.

(Analysis of Substance)

The zinc complex according to the present embodiment can be used as an additive for analysis of a substance having an anionic substituent or a phosphorylated substance. In addition, the complex according to the present embodiment can be used in an analysis method for a substance having an anionic substituent or a phosphorylated substance. Examples of analysis methods for a substance having an anionic substituent or a phosphorylated substance include mass spectrometry, electrophoresis, nuclear magnetic resonance, and chromatography.

For example, when a phosphorylated substance is analyzed, pH of a solution containing a substance to be analyzed is adjusted, and then subjected to mass spectrometry, electrophoresis, nuclear magnetic resonance, or chromatography by a general method. The result is used as a control. Then, $A^−\text{-}Zn_2L$ is intimately mixed with the same solution as that used for obtaining a control, and analyzed in the same manner. The two results of the analyses are compared with each other to find a difference, so that the phosphorylated substance can be analyzed.

The reasons that a difference is found are as follows: The reason that the analysis can be made by mass spectrometry or chromatography resides in that, when the complex is bound to a substance to be analyzed, the molecular weight of the substance to be analyzed is increased by the molecular weight of the complex. For example, when the complex of formula (Ib) is bound to a substance, the molecular weight of the substance is increased by about 800 Da.

The reason that the analysis can be made by electrophoresis resides in that, when the complex is bound to a substance to be analyzed, the charge of the substance to be analyzed is increased by +3. For example, when the complex is bound to a substance to be analyzed having a divalent phosphate group, the charge of the substance is changed from −2 to +1. Therefore, in two-dimensional electrophoresis, changing of spot according to the isoelectric direction or the mass change is expected. Thus, by using the complex, the presence of a phosphorylated peptide or protein can be easily known by a conventional analytical system.

The reason that the analysis can be made by nuclear magnetic resonance resides in that, when the complex is bound to a substance to be analyzed, the chemical shift changes.

Further, when substituent R in the complex is made a higher alkyl group and the inside of a capillary is oil-soluble, the complex can be utilized in capillary liquid chromatography.

The above-mentioned additive for analysis and analysis method can be used in phosphorylated biological substances. Phosphorylation and dephosphorylation of proteins are one of important themes of studies on the information transmission in living bodies and have close relation to the vital functions. In addition, elucidation of the process of such phosphorylation is a main task in the post-genome research, and has attracted attention as a target of drug preparation.

Figure 6:
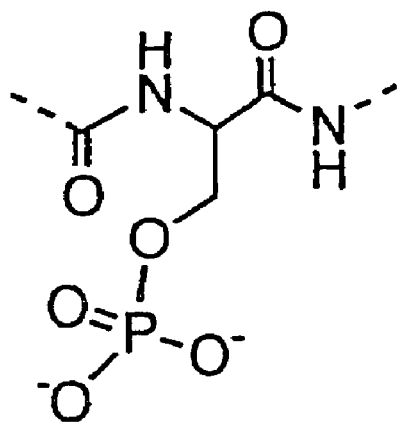
FIG. 6 is a view showing phosphorylated serine.
Figure 7:
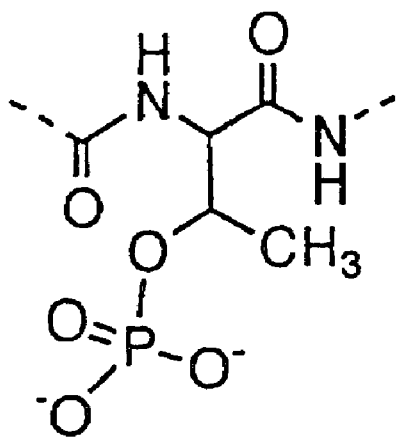
FIG. 7 is a view showing phosphorylated threonine.
Figure 8:
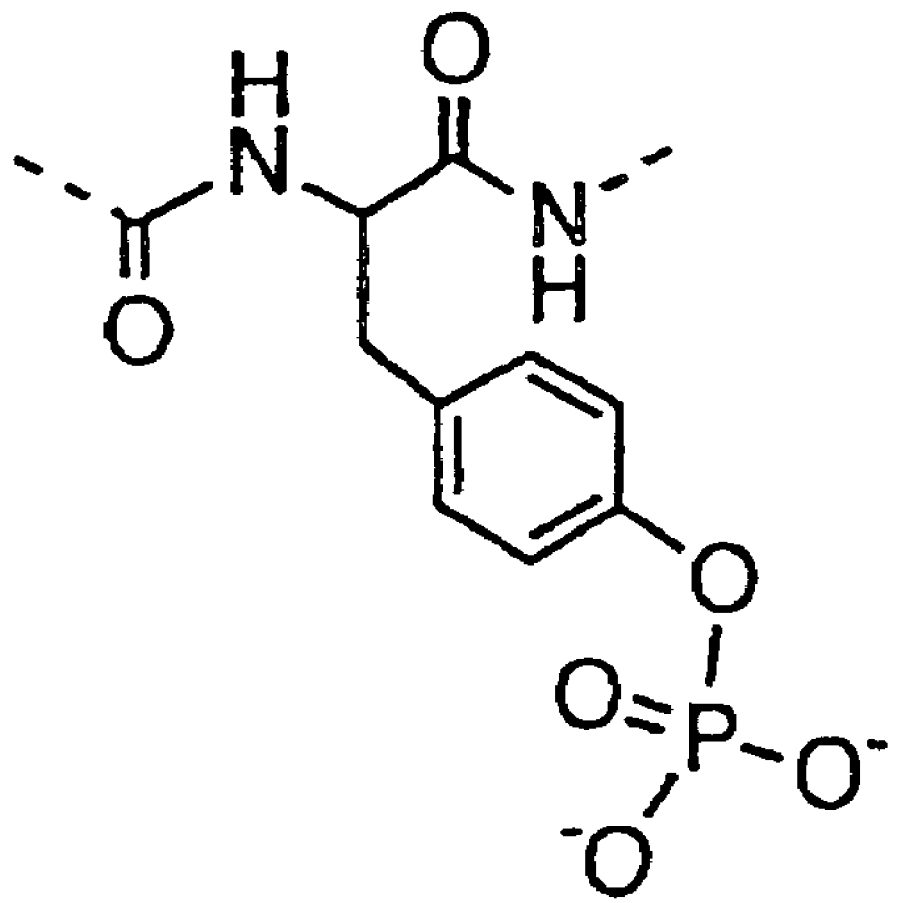
FIG. 8 is a view showing phosphorylated tyrosine.

Here, phosphorylation and dephosphorylation of a biological substance are briefly described. In phosphorylation and dephosphorylation of a biological substance, a variety of enzymes serve as catalysts. Generally, an enzyme for phosphorylation is called kinase. In the phosphorylation of a protein by a kinase, amino acid residues phosphorylated include serine (Ser), threonine (Thr), and tyrosine (Tyr). As shown in FIGS. 6 to 8, a divalent phosphate group (phosphate monoester dianion) is bound to a phosphorylated amino acid residue. Polynucleotide kinase is an enzyme which serves as a catalyst in the reaction for rearrangement of γ phosphate of ATP (adenosine triphosphate) to the OH group of a polynucleotide at a 5′ terminal.

An enzyme which eliminates a phosphate group from a phosphorylated biological substance by hydrolysis is generally called phosphatase. For example, LAR phosphatase or Yop phosphatase eliminates a phosphate group from phosphorylated tyrosine. γ Phosphatase is an enzyme which serves as a catalyst in the reaction for elimination of a phosphate group from each of phosphorylated Ser, Thr, and Tyr.

Alkaline phosphatase extracted from *Escherichia coli* is a dimer comprised of two subunits with 94 kDa, which is an enzyme catalyzing hydrolysis of various phosphates. It is known that two zinc ions in this enzyme are positioned at a space of about 4 angstroms (about $4 \times 10^{-10}$ m). Phosphorylation and dephosphorylation of biological substances are important in vital functions, and elucidation of the process of phosphorylation is a main task in the post-genome research.

As methods for analyzing a phosphorylated biological substance, a method using enzyme-linked immunosorbent assay and a method using a radioisotope have conventionally been known.

Enzyme-linked immunosorbent assay (ELISA) is the method described below. First, an antibody (or antigen) which specifically binds to a desired substance to be analyzed is prepared. Then, a support having a satisfactory amount of the antibody immobilized thereon is reacted with a solution containing the desired substance. This reaction causes the desired substance to be bound to the antibody. Then, the amount of the substance bound to the antibody or the amount of the antibody which is not bound to the substance is measured using an enzyme. The analysis of a phosphorylated biological substance in this way is enzyme-linked immunosorbent assay.

In the above method, an antibody recognizes the molecular structure of a desired substance as a binding site. As a result, this method can be used for analysis of a phosphorylated substance. Further, in the above method, the use of an enzyme makes it possible to detect the bound substance with high sensitivity. Therefore, the method has an advantage in that a desired substance even in a slight amount can be detected.

However, the above method utilizes the action of an antibody which specifically binds to a desired substance, and therefore a specific antibody for the desired substance must be prepared. In the preparation of an antibody, there is a need to obtain and purify a great amount of the desired substance. Further, the preparation of an antibody uses immune response of an animal and hence requires a prolonged period of time. Further, a general antibody recognizes a desired substance, and hence the desired substance is required to have a molecular weight of about several ten thousand Da. Accordingly, when the desired substance has a molecular weight as small as several kDa or less, e.g., a divided protein fragment (peptide), an antibody for a phosphorylated site in the molecular structure cannot be prepared. Thus, it is difficult to use enzyme-linked immunosorbent assay when a desired substance has a molecular weight of several kDa or less.

By using an additive for analysis comprising the complex according to the present embodiment, a phosphorylated substance can be analyzed without using enzyme-linked immunosorbent assay. As a result, there is no need to prepare the above-mentioned antibody. In addition, even when a desired substance has a molecular weight as small as several kDa or less, a phosphorylated site in the desired substance can be detected using the above capturing agent.

The method for analyzing a phosphorylated biological substance using a radioisotope is as follows: In this method, radioisotope $^{32}P$ is used. Generally, a target substance is phosphorylated by [γ-$^{32}$P] ATP substituted by a radioisotope at a γ-position. Then, using a phosphocellulose filter which is one of ion-exchange membranes, the radioactive phosphate in a solution containing the desired substance is replaced by an anion in the filter to capture the radioactive phosphate. Then, the filter is washed with an acid to remove excess [γ-$^{32}$P] ATP. Then, the amount of radioactive phosphorus remaining in the filter is quantitatively determined by a radiation counter. A phosphorylated biological substance is analyzed by the quantitative determination in this method.

The phosphocellulose filter is, for example, a filter disclosed in "Isolation of Phosphorylated Peptides and Proteins on Ion Exchange Papers, D. B. Glass et al, Anal. Biochem. 87, p. 566-575 (1978)" or Japanese Unexamined Patent Publication No. 2000-316599.

In the above method using a radioisotope, radiation is used and hence a measurement with extremely high sensitivity can be made. However, this method uses a radioisotope and therefore requires cumbersome management of waste liquor. In addition, equipment for using radiation must be prepared.

Instead of the method using a radioisotope, by employing the method using a capturing agent comprising the complex, the above-mentioned cumbersome management of waste liquor is not required. Needless to say, radiation is not used in the method using a capturing agent comprising the complex and hence, there is no need to prepare equipment for using radiation.

In the conventional analysis methods, there is a further task in the analysis of a sample which is not confirmed to contain a phosphorylated substance. For example, for elucidating the functions of a protein, two-dimensional electrophoresis is used. Peptides formed by dividing a protein using a protease are separated on a gel by isoelectric points or masses to form specific spots for the respective peptides. A phosphorylated peptide and a peptide which is not phosphorylated have different charges. Therefore, two-dimensional electrophoresis can separate the phosphorylated peptide and the non-phosphorylated peptide from each other. However, when a number of spots are formed, the phosphorylated peptide cannot be identified. In the electrophoresis of a phosphorylated protein synthesized using ATP labeled with a radioisotope, a phosphorylated peptide can be identified and separated by detecting radiation of the spots. However, this method has problems of handling of radiation similar to those of the above method. Liquid chromatography and nuclear magnetic resonance have similar problems of this kind.

By using an additive for analysis comprising the complex according to the present embodiment, a phosphorylated peptide and a non-phosphorylated peptide can be separated from each other in two-dimensional electrophoresis, and problems of handling of radiation can be avoided.

(Control of Reaction)

The complex according to the present embodiment can be used as a component of a phosphorylated-substance deactivating agent for deactivating a phosphorylated substance.

The complex according to the present embodiment binds to a phosphorylated site of, e.g., an amino acid. When the complex binds to such a site, the complex caps the phosphorylated site. Formation of the capping suppresses a reaction of a substance having the phosphorylated site and another substance, lowering the biological activity of the phosphorylated substance.

The complex according to the present embodiment has a property such that it strongly binds to a phosphorylated site. Further, the complex releases almost no zinc ions under neutral conditions and hence has a small effect on a human body. For this reason, the phosphorylated-substance deactivating agent according to the present embodiment can be utilized as, for example, a drug for treatment of hyperphosphatemia. By using the complex in a drug for treatment of hyperphosphatemia, it can be expected that the drug exhibits remarkable effect by administration in a small amount and causes almost no side effect.

The complex according to the present embodiment can be used as a component of a phosphatase inhibitor.

The complex according to the present embodiment binds to a phosphorylated site of a protein or a nucleotide to cap the phosphorylated site. The capping temporarily inhibits a phosphatase from functioning.

The phosphatase inhibitor according to the present embodiment can be utilized in the following application. For example, when a phosphorylated site of an amino acid or a protein is inhibited from undergoing dephosphorylation, the complex according to the present embodiment is added to cap the phosphorylated site, making it possible to temporarily inhibit a phosphatase from functioning. By adding a metal chelating agent, such as EDTA (ethylenediaminetetraacetic acid), or adjusting the pH, the enzyme activity of the phosphatase temporarily inhibited can be recovered. By utilizing the phosphatase inhibitor, for example, presence or absence of a novel phosphatase and the activity of a phosphatase can be examined.

Compounds comprising the complex appropriately modified and isomers of the complex can be synthesized. Therefore, when utilizing the complex in the phosphatase inhibitor, the complex according to the present embodiment can be utilized as it is, a compound obtained by appropriately modifying the complex can be utilized, or an isomer of the complex can be utilized.

EXAMPLES

Example 1

Synthesis of Zinc Complex

The compounds of formula (Ib) and formula (IIIb) were synthesized by the following method.

To an ethanol solution (3 ml) of zinc acetate (1.0 mmol) was added a methanol solution (3 ml) of TMAHP as an o-methyl type ligand at room temperature. Then, while stirring by means of, e.g., a magnetic stirrer, to the resultant mixed solution were added sodium hydroxide (0.5 mmol) and sodium perchlorate (2.0 mmol). A pH of the solution was measured and adjusted so that the pH of the solution was close to 7.0. Then, the resultant colorless solution was concentrated to obtain a white solid of $Zn_2L$ (o-methyl type)-acetate $(ClO_4)_2$ at a yield (0.39 g) of 87%, wherein $(ClO_4)_2$ is a counter anion.

The chemical structure of the white solid was confirmed by elemental analysis, $^1$H-NMR (400 MHz), $^{13}$C-NMR (100 MHz), and infrared analysis. The data are shown below.

In the elemental analysis, the theoretical elemental value is: $C_{33}H_{40}N_6O_{11}CL_2Zn_2$: C, 44.12; H, 4.49; N, 9.35, and the elemental value measured was: C, 44.04; H, 4.51; N, 9.48.

The results of $^1$H-NMR were as follows: $^1$H-NMR ($CD_3CN$ solvent, 400 MHz): δ=2.23 (3H, s, $CH_3COO$), 2.27 (2H, t, $CH_2N$), 2.78 (6H, s, $pyCH_3$), 2.80 (6H, s, $pyCH_3$), 3.02 (2H, dd, $CH_2N$), 3.71 (2H, d, $NCH_2py$), 4.02 (2H, d, $NCH_2py$), 4.07 (2H, d, $NCH_2py$), 4.14 (1H, m, CH), 4.46 (2H, d, $NCH_2py$), 7.22 (2H, d, pyH), 7.33 (2H, d, pyH), 7.36 (2H, d, pyH), 7.41 (2H, d, pyH), 7.86 (2H, t, pyH), 7.88 (2H, t, pyH).

The results of $^{13}$C-NMR were as follows: $^{13}$C NMR ($CD_3CN$ solvent, 100 MHz): δ=24.6 ($pyCH_3$), 24.7 ($pyCH_3$), 25.8 ($CH_3$—), 55.4 ($CH_2N$), 58.4 ($NCH_2py$), 58.7

(NCH$_2$py), 62.6 (CH), 122.9 (py), 123.2 (py), 126.6 (py), 126.7 (py), 141.7 (py), 142.0 (py), 156.5 (py), 160.4 (py), 161.0 (py), 180.8 (COO).

The results of the infrared analysis were as follows: IR (cm$^{-1}$): $\nu_{as}$(COO), 1,576; $\nu_s$(COO), 1,440; $\nu_3$(ClO$_4$), 1,086.

The above data indicates that the white solid is a substance comprising the compound of formula (Ib) and an acetate anion which are bound together in a 1:1 ratio, and having, as a counter ion, a perchlorate ion in an amount two times the mole of the compound of formula (Ib).

Example 2

Synthesis of Zinc Complex

The compounds of formula (Ia) and formula (IIIa) were synthesized by the following method.

To an ethanol solution (100 ml) of TPAHP (4.39 mmol) as a H type ligand was added a 10 M aqueous solution of sodium hydroxide (1.0 eq), and then zinc acetate dihydrate (9.66 mmol, 2.2 eq) was added thereto. The solvent was removed under reduced pressure to obtain a brown oil residue. Water (10 ml) was added to the residue to dissolve it, and a 1.0 M aqueous solution of sodium perchlorate (3.0 eq) was added dropwise to the resultant solution while heating. A milky white crystal was precipitated. The crystal was collected by filtration, and dried by heating to obtain a white solid of Zn$_2$L (H type)-acetate (ClO$_4$)$_2$ as a slightly yellowish brown powdery crystal at a yield (2.99 g) of 79%, wherein (ClO$_4$)$_2$ is a counter anion.

The chemical structure of the white solid was confirmed by elemental analysis, $^1$H-NMR (400 MHz), $^{13}$C-NMR (100 MHz), and infrared analysis. The data are shown below.

In the elemental analysis, the theoretical elemental value is: C$_{29}$H$_{34}$N$_6$O$_{12}$CL$_2$Zn$_2$: C 40.49; H 3.98; N 9.77, and the elemental value measured was: C 40.43; H 3.86; N 9.85. The results of $^1$H-NMR were as follows: $^1$H NMR (DMSO-D$_6$ solvent, 400 MHz): δ=2.04 (2H, dd, J=12.1 and 12.4 Hz, HC-1,3), 2.53 (3H, s, HC-35), 3.06 (2H, dd, J=12.1 and 12.3 Hz, HC-1,3), 3.74 (1H, t, J=10.4 Hz, HC-2), 4.02-4.34 (8H, m, HC-5,13,20,27), 7.54-7.65 (8H, m, HC-10,11,18,19,25, 26,32, 33), 8.06-8.12 (4H, m, HC-9,17,24,31), 8.58 (4H, dd, J=16.3 and 16.5 Hz, HC-8,16,23,30)

The results of $^{13}$C-NMR were as follows: $^{13}$C NMR (DMSO-D$_6$ solvent, 100 MHz): δ=58.0, 60.1, 62.0, 64.6, 122.7, 124.3, 124.4, 139.9, 140.4, 147.0, 147.2, 154.7, 155.1.

The results of the infrared analysis were as follows: IR (cm$^{-1}$): $\nu_{as}$(COO), 1,556; $\nu_3$ (ClO$_4$), 1,090.

The above data indicates that the white solid is a substance comprising the compound of formula (Ia) and an acetate anion which are bound together in a 1:1 ratio, and having, as a counter ion, a perchlorate ion in an amount two times the mole of the compound of formula (Ia).

Example 3

Mass Spectrometry 1

A complex of 4-nitrophenylphosphate monoester anion bound to Zn$_2$L (o-methyl type) was subjected to mass spectrometry (TOF-Mass analysis).

To a water/acetonitrile (1:1) solution (0.1 mM) of the compound (Zn$_2$L (o-methyl type)-acetate) represented by formula (Ib) was added 4-nitrophenylphosphate monoester anion equimolar to the compound represented by formula (Ib) to prepare a sample solution. In analysis of the sample solution, an electro-spray ionization mass spectrometer (ESI-MS)(LCT type), manufactured by Micromass, was used. The results are shown in FIGS. 9 and 10.

Figure 9:
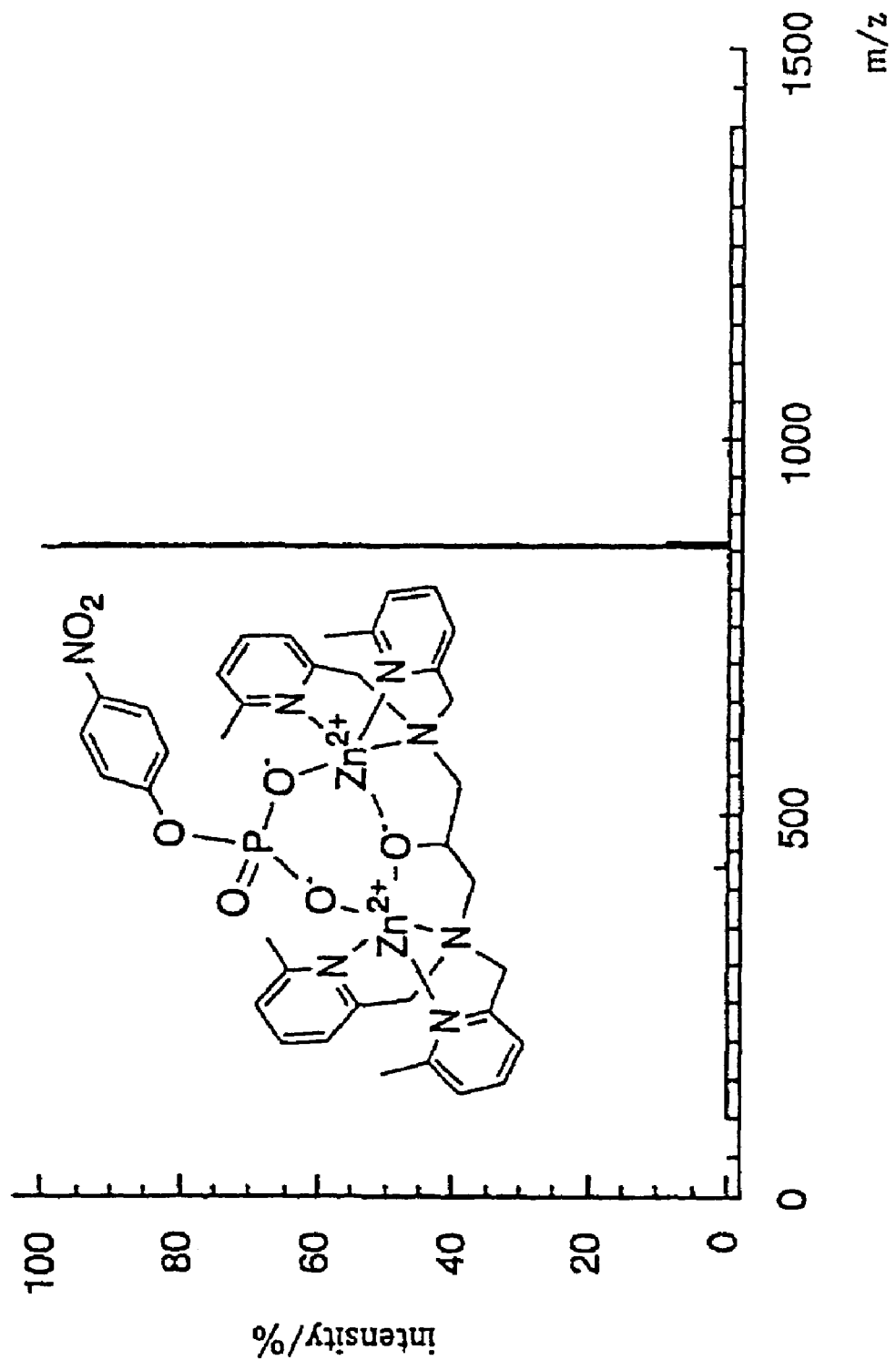
FIG. 9 is a diagram showing the results of mass spectrometry (m/z: 0 to 1,500) with respect to the composite of the zinc complex (Ib) of the present invention bound to a 4-nitrophenylphosphate monoester anion.
Figure 10:
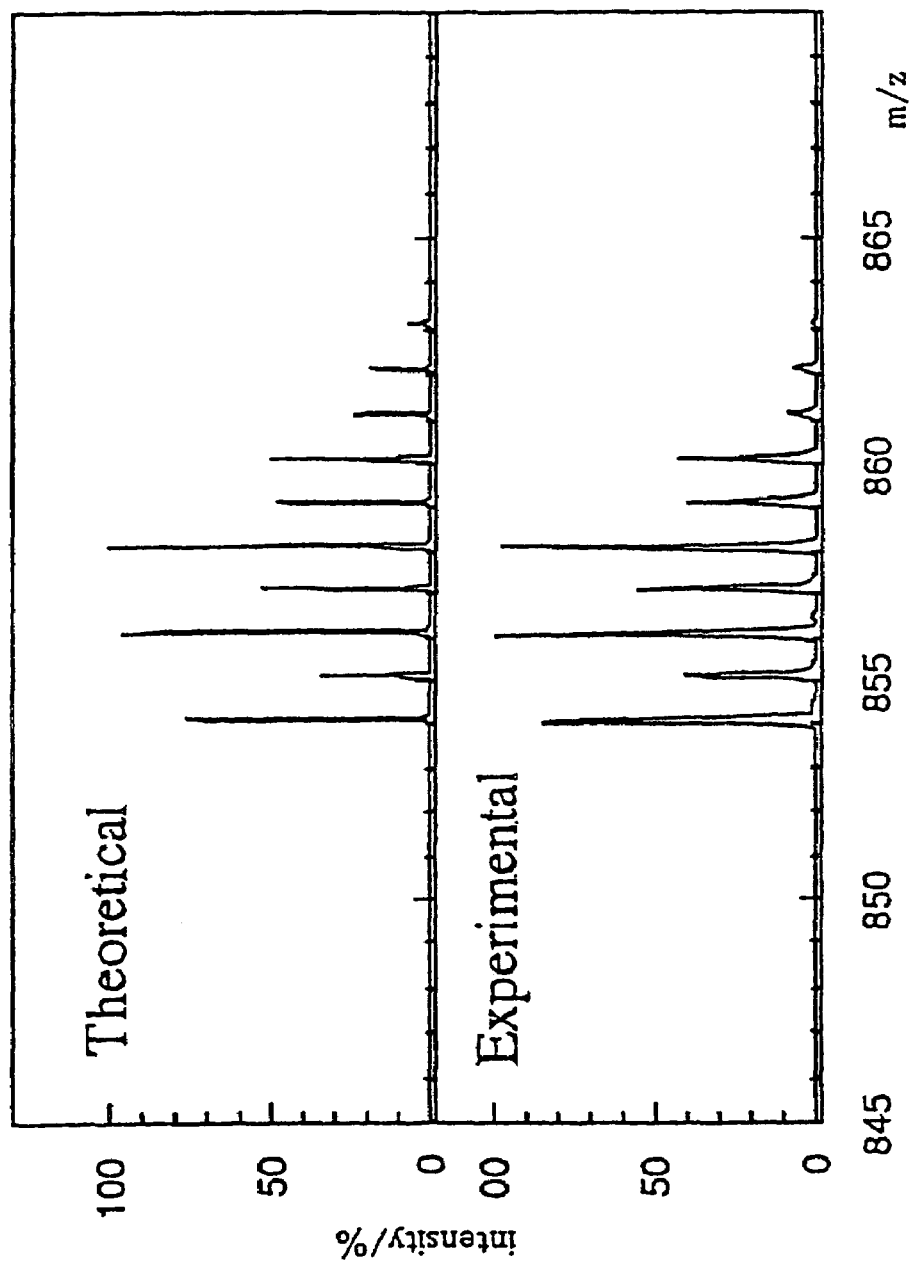
FIG. 10 is a diagram showing the results of mass spectrometry (m/z: 845 to 870) with respect to the composite of the zinc complex (Ib) of the present invention bound to a 4-nitrophenylphosphate monoester anion.

From the results shown in FIGS. 9 and 10, it has been found that the acetate anion bound to Zn$_2$L (o-methyl type) was quantitatively replaced by 4-nitrophenylphosphate monoester anion. That is, the replacement caused a peak ascribed to the Zn$_2$L (o-methyl type) complex to which 4-nitrophenylphosphate monoester anion was bound.

The peaks indicated by "Theoretical" in FIG. 10 are theoretical analysis peaks prepared based on the structural formula shown in FIG. 9. The theoretical analysis peaks were determined by making calculation from stable isotopes of zinc and carbon ($^{64}$Zn, $^{66}$Zn, $^{67}$Zn, $^{68}$Zn, $^{70}$Zn; $^{12}$C, $^{13}$C) and the isotopic abundance. The peaks indicated by "Experimental" in FIG. 10 are experimentally obtained. From these peaks, it has been found that the theoretical analysis peaks are substantially consistent with the peaks experimentally obtained.

When a 4-nitrophenylphosphate monoester anion is not phosphorylated, that is, 4-nitrophenol and inorganic phosphate ions are present, two peaks having different molecular weights appear. The two peaks are ascribed to a complex to which a hydrogenphosphate ion is bound and a free zinc complex. Therefore, using simple mass spectrometry and the zinc complex, presence or absence of phosphorylation can be quickly and easily confirmed.

Example 4

Mass Spectrometry 2

A complex of phosphorylated serine bound to Zn$_2$L (o-methyl type) was subjected to mass spectrometry (Tof-Mass analysis).

To a water/acetonitrile (1:1) solution (0.1 mM) of the compound (Zn$_2$L (o-methyl type)-acetate) represented by formula (Ib) was added phosphorylated serine (minus divalent, disodium salt; manufactured by Sigma Chemical Company) equimolar to the compound represented by formula (III) to prepare a sample solution. In analysis of the sample solution, an electro-spray ionization mass spectrometer (ESI-MS)(LCT type), manufactured by Micromass, was used. The results are shown in FIG. 11.

Figure 11:
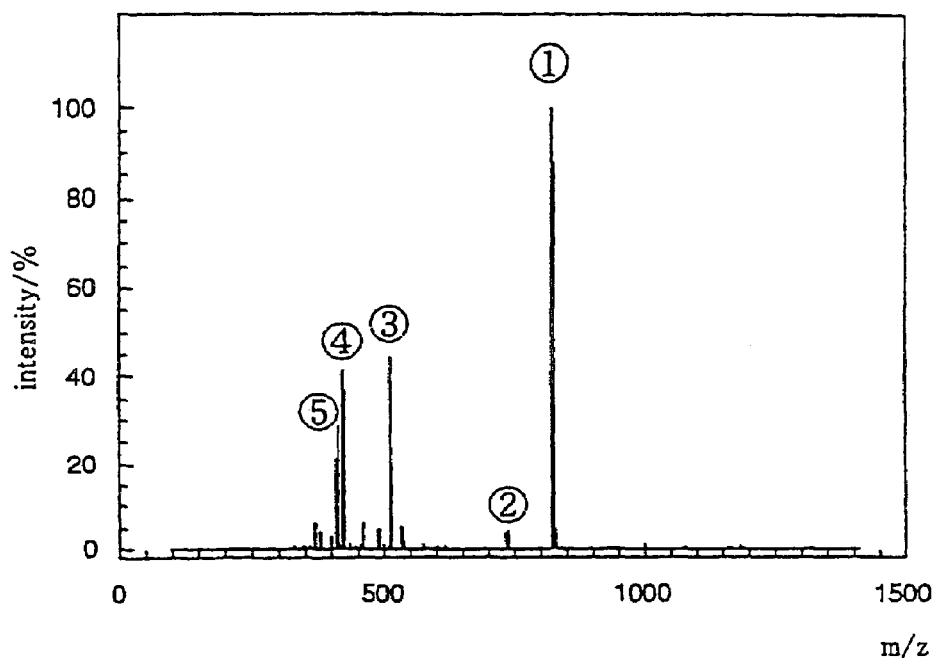
FIG. 11 is a diagram showing the results of mass spectrometry (m/z: 0 to 1,500) with respect to the compound of the zinc complex (Ib) of the present invention bound to phosphorylated serine.
Figure 11:
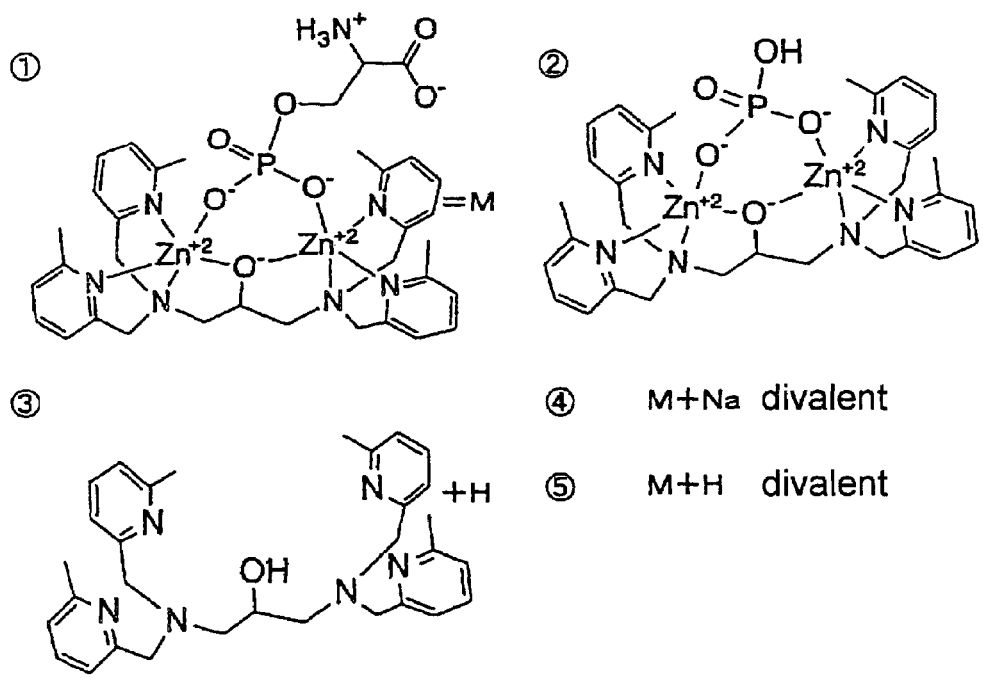

From the results shown in FIG. 11, it has been found that the acetate anion bound to Zn$_2$L (o-methyl type) was quantitatively replaced by phosphorylated serine as expected. The analysis peaks indicated by (1) to (5) in FIG. 11 are ascribed to, respectively, compounds (1) to (5) shown in FIG. 11. The analysis peak (1) (around 820) is ascribed to the complex of phosphorylated serine bound to Zn$_2$L (o-methyl type).

Example 5

Mass Spectrometry 3

The compound represented by formula (Ia) was individually added to various kinds of phosphorylated anions and subjected to mass spectrometry using a matrix assisted laser desorption/ionization time-of-flight mass spectrometer (MALDI-TOF/MS).

MALDI-TOF/MS: Voyager RP model (manufactured by PE Biosystems Inc.)

Additive: Compound represented by formula (Ia)

Sample: p60c-src Peptide 521-533, phosphorylated type and non-phosphorylated type*, O-Phospho-L-serine sodium salt Matrix: THAP (2,4,6-trihydroxyacetophenone) 40 mg/ml ($CH_3CN$)

pH Buffer for dissolving a sample: 10 mM $Tris-H_3BO_3$ buffer (pH=8.0)

Figure 12:
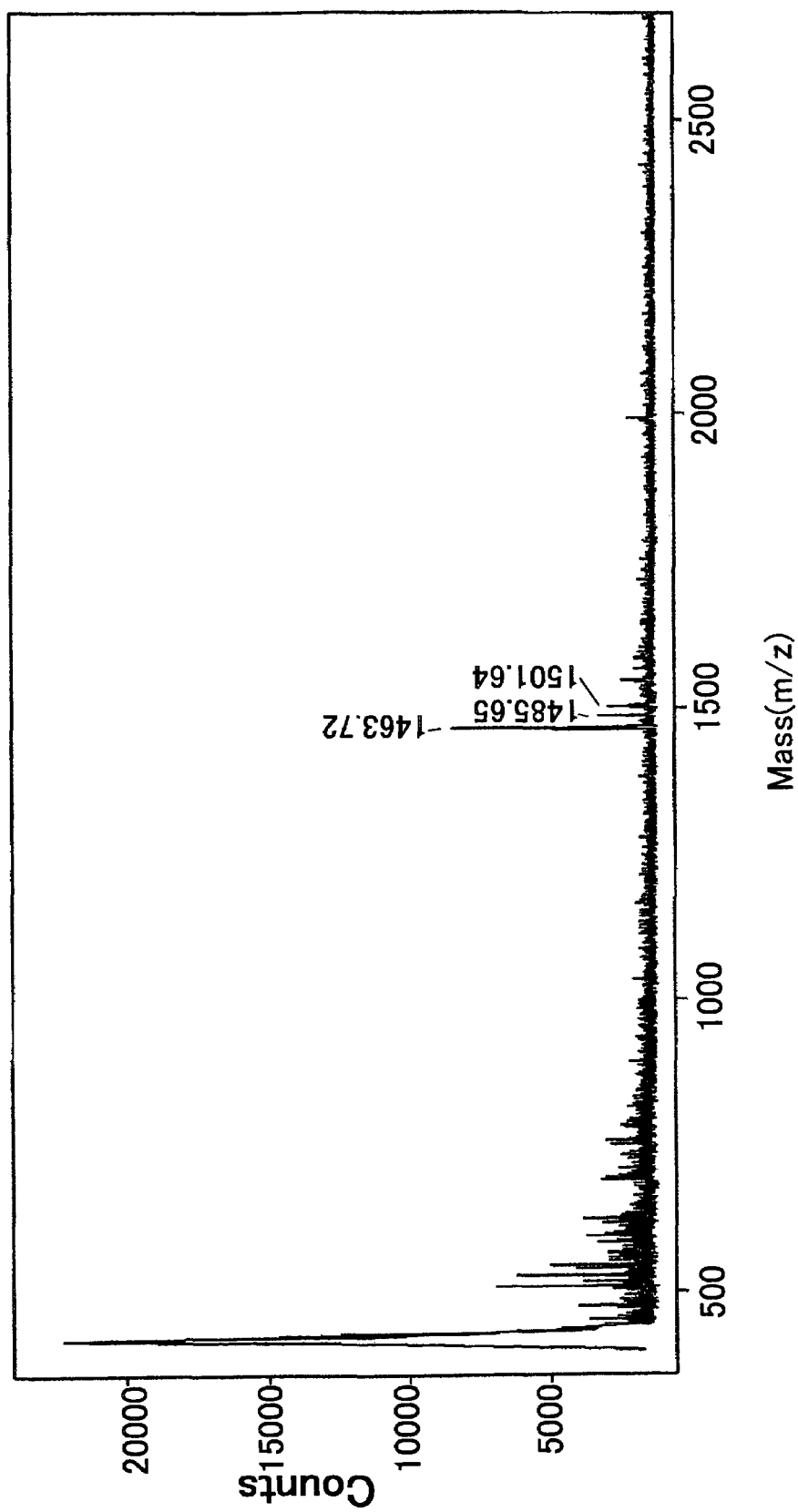
FIG. 12 is a diagram showing the results of MALDI-TOF/MS analysis with respect to a phosphorylated peptide and a non-phosphorylated peptide without using the zinc complex of the present invention.
Figure 13:
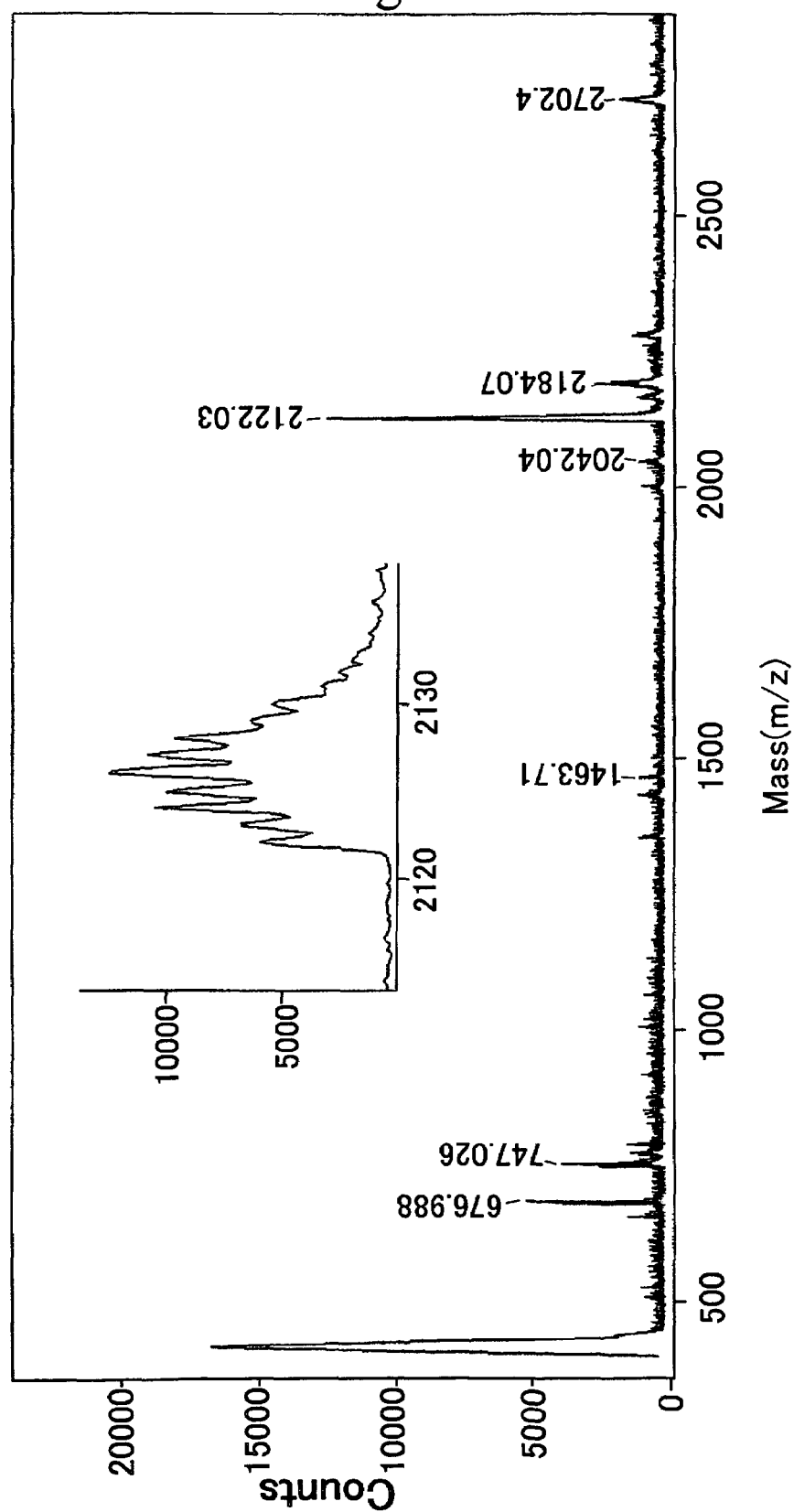
FIG. 13 is a diagram showing the results of MALDI-TOF/MS analysis with respect to each of the peptides in FIG. 12 to which the zinc complex of the present invention is added.

Preparation of a Sample for Measurement and Measurement Method:

The compound (1 mM) represented by formula (Ia) and each sample (1 mM, * is 2 mM) were individually dissolved in distilled water. Sample solutions for MALDI-TOF/MS measurement having the compositions below were prepared by mixing in a 1.5-mL microtube. The total volume of the 1 mM compound represented by formula (Ia) (5 μL), an aqueous sample solution (10 μL), a 10 mM Tris-borate buffer (pH=8.0) (30 μL), and distilled water (5 μL) was 50 μL. 0.5 μL of a sample for measurement was applied to a sample plate, and then immediately 0.5 μL of a matrix solution was added to the resultant droplet. The solvent was removed by air-drying at room temperature, followed by measurement of mass spectrometry. The results of the analysis with respect to p60c-src Peptide 521-533 phosphorylated type and non-phosphorylated type are shown in FIGS. 12 to 14, and the results with respect to the O-Phospho-L-serine sodium salt are shown in FIG. 15. The Phos-tag complex in the figure corresponds to the compound represented by formula (Ia). As a result, by using the analysis method and zinc complex in the present Example, a phosphorylated compound can be measured with high sensitivity in the physiological pH range.

Example 6

$^{31}$P) Nuclear Magnetic Resonance

A complex of 4-nitrophenylphosphate monoester anion bound to $Zn_2L$ (o-methyl type) was subjected to $^{31}$P nuclear magnetic resonance.

To a heavy water/heavy acetonitrile (1:1) solution (5.0 mM) of the compound ($Zn_2L$ (o-methyl type)-acetate) represented by formula (Ib) was added 4-nitrophenylphosphate monoester anion equimolar to the compound represented by formula (Ib) to prepare a sample solution. The sample solution was subjected to analysis using a nuclear magnetic resonance analyzer, LA500 (manufactured by JEOL LTD.). The temperature for the analysis was 35° C.

When 4-nitrophenylphosphate monoester anion was not bound to the zinc complex, the phosphorus nucleus exhibited a peak δ=2.74 ppm. However, from the results of the above analysis, it has been found that, when 4-nitrophenylphosphate monoester anion is bound to the zinc complex, the phosphorus nucleus exhibits a sharp peak δ=0.55 ppm, which shifts to the higher magnetic field side than that obtained when 4-nitrophenylphosphate monoester anion is not bound to the zinc complex. As a reference, an 80% aqueous phosphate solution (δ=0 ppm) was used.

Example 7

Electrophoresis 1

A complex of phosphorylated tyrosine bound to $Zn_2L$ (o-methyl type) was subjected to electrophoresis.

To a water/acetonitrile (1:1) solution (5 mM) of the compound ($Zn_2L$ (o-methyl type)-acetate) represented by formula (Ib) was added phosphorylated tyrosine (minus divalent, disodium salt; manufactured by Sigma Chemical Company) equimolar to the compound represented by formula (Ib). Then, the solvent was removed by vacuum evaporation to obtain a white solid. The white solid was dissolved in a small amount of water to prepare a sample solution.

In electrophoresis, an electrophoresis machine, SJ-1051 V-C stabilizer (manufactured by ATTO Corporation) was used. As an electrolytic solution, a 50 mM-pH 7.4 HEPES buffer aqueous solution was used. As an electrophoresis membrane, 6×12 cm cellulose acetate paper (Gelman Science Seprahore III) as used. As a reference, a standard reagent Bromophenol Blue (minus monovalent) and phosphorylated tyrosine to which the complex was not bound were used. As a coloring agent for phosphorylated tyrosine, a 1% aqueous ninhydrin solution was used. Electrophoresis was conducted under conditions such that the temperature was room temperature, the voltage of electrophoresis was 300 V, and the period of time for migration was 5 minutes. The results are shown in FIG. 16.

In FIG. 16, character a designates phosphorylated tyrosine, character b designates a complex of phosphorylated tyrosine bound to $Zn_2L$ (o-methyl type), and character c designates Bromophenol Blue. As shown in FIG. 16, a and c were negatively charged and hence migrated toward the positive electrode. In contrast, b migrated toward the negative electrode. The reason that b migrated toward the negative electrode resides in that the complex of phosphorylated tyrosine (−2) bound to $Zn_2L$ (o-methyl type) (+3) is positively (+1) charged.

Example 8

Electrophoresis 2

Double-stranded DNAs having different lengths (587 to 51 pb), which had been treated with an acid phosphatase (DNAs having no phosphate group at the 5' terminal, 5'-OH) and not been treated (5'-P), were subjected to electrophoresis on the same gel, and stained with ethidium bromide. The results are shown in FIG. 17. The "Phos-tag 1" in the figure corresponds to the compound represented by formula (Ia).

In (A) shown in the figure, a general buffer (Trisborate) for electrophoresis was used. When 10 μM of the compound represented by formula (Ia) was added, all the DNAs having a phosphate group were small in the distance of migration, indicating that the compound represented by formula (Ia) was bound to the terminal phosphate group to serve as an anchor.

In (B) shown in the figure, a pH buffer containing excess inorganic phosphate ions was used. A difference in the distance of migration as seen in (A) is not found. The reason for this is that inorganic phosphate ions competitively bind to the compound represented by formula (Ia), so that the compound represented by formula (Ia) cannot bind to the terminal phosphate group.

The result indicates that a DNA having a phosphate group and a DNA having no phosphate group and having the same length as that of the DNA having a phosphate group can be separated from each other by electrophoresis. In addition, the compound represented by formula (Ia) bound to a phosphorylated molecule can be easily removed by adding inorganic phosphate ions.

Example 9

Electrophoresis 3

Casein having eight serine residues phosphorylated and one obtained by removing the phosphate groups from the above casein were separated by polyacrylamide electrophoresis, and stained with Coomassie Brilliant Blue. The conditions for the electrophoresis and the results are shown in FIG. 18. Bovine serum albumin was used as a protein for comparison. The "Phos-tag 1" in the figure corresponds to the compound represented by formula (Ia).

In a control experiment in which the compound represented by formula (Ia) was not used, the phosphorylated casein, which was more negatively charged electrically, migrated more rapidly to the positive electrode (electrophoresis diagram A). On the other hand, when 20 µM of the compound represented by formula (Ia) was added (electrophoresis diagram B), the compound represented by formula (Ia) having a +3 valence was bound to the phosphate group, so that the position of the phosphorylated casein and the position of the non-phosphorylated casein in the electrophoresis were reversed.

The result indicates that the position of a phosphorylated protein in electrophoresis can be arbitrarily changed under physiological conditions.

Example 10

Electrophoresis 4

Using casein having five serine residues phosphorylated as a substrate, an effect of addition of the compound represented by formula (Ia) in the dephosphorylation reaction by potato acid phosphatase (PAP) was examined. The phosphorylated casein and the dephosphorylated casein were separated by SDS polyacrylamide electrophoresis, and stained with Coomassie Brilliant Blue. The conditions for the electrophoresis and the results are shown in FIG. 19. The "Phos-tag" in the figure corresponds to the compound represented by formula (Ia).

It has been found that, as the concentration of the compound represented by formula (Ia) increases (see 2 to 8 in the figure), the dephosphorylation reaction is inhibited. The reason that a plurality of bands appear is that caseins having different numbers of serine residues phosphorylated (intermediates in the dephosphorylation reaction) are present.

The result indicates that the compound represented by formula (Ia) can control various reactions to which a phosphate group relates.

The invention claimed is:

1. A zinc complex represented by a formula (I-0)

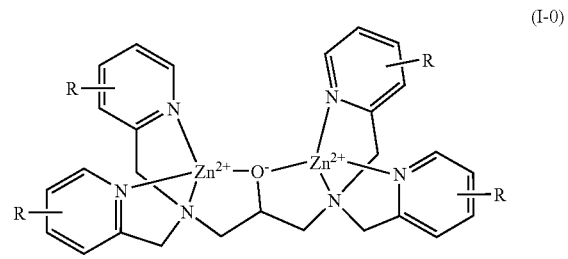

(I-0)

wherein each R is the same or different from each other and each R represents H; an alkyl group having 1 to 16 carbon atoms; an acyl group, a carboxyalkyl group, an acylalkyl group, a carbamoylalkyl group, a cyanoalkyl group, a hydroxyalkyl group, an aminoalkyl group or a haloalkyl group, wherein an alkyl portion of said acyl group, said carboxyalkyl group, said acylalkyl group, said carbamoylalkyl group, said cyanoalkyl group, said hydroxyalkyl group, said aminoalkyl group and said haloalkyl group has 1 to 16 carbon atoms; a carboxyl group; a carbamoyl group; a hydroxyl group; a cyano group; an amino group; or a halogeno group, provided that the case where each R is hydrogen is excluded, the zinc complex is capable of capturing a substance having one or more anionic substituents.

* * * * *